US012779704B2

(12) United States Patent
Sebring

(10) Patent No.: US 12,779,704 B2
(45) Date of Patent: Nov. 3, 2026

(54) COUPLER FOR ROBOTIC END EFFECTOR

(71) Applicant: Stryker Corporation, Portage, MI (US)

(72) Inventor: Paul Sebring, Townsend, MA (US)

(73) Assignee: Stryker Corporation, Portage, MI (US)

( * ) Notice: Subject to any disclaimer, the term of this patent is extended or adjusted under 35 U.S.C. 154(b) by 456 days.

(21) Appl. No.: 18/211,785

(22) Filed: Jun. 20, 2023

(65) Prior Publication Data

US 2023/0404686 A1 Dec. 21, 2023

Related U.S. Application Data

(60) Provisional application No. 63/353,964, filed on Jun. 21, 2022.

(51) Int. Cl.
*B25J 15/04* (2006.01)
*A61B 17/00* (2006.01)

(52) U.S. Cl.
CPC ........... *B25J 15/04* (2013.01); *B25J 15/0408* (2013.01); *B25J 15/045* (2013.01); *A61B 2017/00477* (2013.01); *B25J 15/0425* (2013.01)

(58) Field of Classification Search
CPC ...... B25J 15/04; B25J 15/0408; B25J 15/045; A61B 2017/00477
See application file for complete search history.

(56) References Cited

U.S. PATENT DOCUMENTS 5,098,253 A * 3/1992 Du .......................... B25J 15/04 901/29
7,725,162 B2 5/2010 Malackowski et al.
8,118,488 B2 2/2012 Gregerson
9,008,757 B2 4/2015 Wu
9,111,379 B2 8/2015 Gregerson et al.
9,119,655 B2 9/2015 Bowling et al.
9,801,592 B2 10/2017 Stanton et al.
9,962,132 B2 5/2018 Gregerson
10,151,810 B2 12/2018 Gregerson et al.
10,456,207 B2 10/2019 Flatt
10,959,783 B2 3/2021 Gregerson et al.
11,103,990 B2 8/2021 Sebring et al.
11,160,620 B2 11/2021 Ebbitt et al.
2014/0275953 A1 9/2014 Gregerson et al.
2020/0078097 A1 3/2020 Gregerson et al.
2022/0410407 A1* 12/2022 Matsumoto .......... B25J 15/0408

* cited by examiner

*Primary Examiner* — Minnah L Seoh
*Assistant Examiner* — Gregory T Prather
(74) *Attorney, Agent, or Firm* — Howard & Howard Attorneys PLLC

(57) ABSTRACT

A coupling system for removably attaching an end effector to a distal end of a surgical robotic arm. The coupling system includes a first coupler portion including a boss coupled to the surgical robotic arm and a second coupler portion coupled to the end effector. The first coupler portion further includes a first alignment pin extending from the boss and having a first configuration, and a second alignment pin extending from the boss in spaced relation from the first alignment pin and having a second configuration different from the first configuration. The second coupler portion includes a socket body defining a receiver with a floor surface. A first alignment socket and a second alignment socket are defined in the floor surface and configured for engagement with the first and second alignment pins.

13 Claims, 18 Drawing Sheets

COUPLER FOR ROBOTIC END EFFECTOR

CROSS-REFERENCE TO RELATED APPLICATION

The subject patent application claims priority to and all the benefits of United States Provisional Patent Application No. 63/353,964 filed on Jun. 21, 2022, the disclosure of which is hereby incorporated by reference in its entirety.

BACKGROUND

Surgical systems are frequently used to assist medical professionals in carrying out various types of surgical procedures. To this end, a surgeon may use a surgical system to guide, position, move, actuate, or otherwise manipulate various tools, components, prostheses, and the like during a surgery. Surgical systems may include surgical robots which can be used to assist surgeons in performing a number of different types of surgical procedures. By way of illustration, surgical robots are commonly used in procedures involving the correction, stabilization, resection, or replacement of one or more parts of a patient's body, such as to help improve patient mobility, reduce pain, mitigate the risk of subsequent injury or damage, and the like.

Certain types of surgical robots may include a robotic arm with an end effector that positions a tool above the patient and along a desired trajectory that is aligned with the desired orientation of the tool relative to a surgical site on the patient. By way of illustrative example, in many types of spinal procedures, a robotic arm of a surgical robot positions a tool guide end effector along the desired trajectory that is aligned with the desired orientation of the tool relative to vertebrae and/or discs of the patient's spine. It will be important that reliably and consistently maintaining alignment relative to the patient's anatomy help ensure that postoperative results match desired preoperative surgical plans.

In some cases, to assist in maintaining proper alignment of the tool guide and the tool relative to the surgical site on the patient, a navigation system is employed. Conventional navigation systems determine a pose of the tool with respect to the patient's anatomy so that the robotic arm can position the tool along the desired trajectory according to the surgeon's plan. To this end, navigation systems may include a localizer and trackers viewable by the localizer and attached to tracked objects so that the robotic system can monitor and respond to movement of tracked objects during the surgical procedure by dynamically moving the tool guide to as needed to maintain the desired trajectory of the tool. Certain types of trackers may include "active" markers defined by light emitting diodes capable of emitting light detectable by the localizer.

In some circumstances, the end effector may need to be removed from the robotic arm to utilize a different end effector having different characteristics, maintenance/repair of the end effector, or because a surgeon may need to view or otherwise access the space occupied by the surgical robot. If the connection between the end effector and the robotic arm is not sufficiently precise, accurately tracking the location of the end effector will be challenging. Similarly, if a removable connection is not repeatable, the navigation system may require recalibration each time the end effector is removed. Tracking the end effector with high precision and accuracy is facilitated by a precise and repeatable connection between the end effector and the robotic arm.

Accordingly, there remains a need in the art for addressing one or more of these deficiencies.

SUMMARY

In one implementation, aspects of a coupling system for removably attaching an end effector to a distal end of a surgical robotic arm. The coupling system comprises a first coupler portion including a boss coupled to the robotic arm. The first coupler portion further includes a first alignment pin extending from the boss and having a first configuration, and a second alignment pin extending from the boss in spaced relation from the first alignment pin and having a second configuration different from the first configuration. The coupling system further comprises a second coupler portion engageable with the first coupler portion. The second coupler portion includes a socket body defining a receiver with a floor surface. The socket body includes a first alignment socket defined in the floor surface and a second alignment socket defined in the floor surface in spaced relation from the first alignment socket. The coupling system further includes a clamp mechanism operatively engageable between the first coupler portion and the second coupler portion and movable between a clamped configuration with the first alignment pin engaged with the first alignment socket and the second alignment pin engaged with the second alignment socket for securing the first coupler portion to the second coupler portion.

In another implementation, aspects of coupling system for removably attaching an end effector to a distal end of a surgical robotic arm. The coupling system comprises a first coupler portion. The first coupler portion includes a boss coupled to the robotic arm, the boss having an upper face and a lower face arranged non-parallel to each other, and an outer face extending between the upper face and the lower face. The first coupler portion further includes a toggle fastener coupled to the outer face and protruding therefrom. The coupling system further comprises a second coupler portion engageable with the first coupler portion. The second coupler portion includes a socket body defining a receiver and a recess. The socket body has an upper receiver wall and a lower receiver wall arranged non-parallel to each other. The coupling system further includes a clamp mechanism operatively engageable between the first coupler portion and the second coupler portion and movable between a clamped configuration and an unclamped configuration. The clamp mechanism includes a clamp member pivotably supported in the recess and engageable with the toggle fastener for securing the first coupler portion to the second coupler portion.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or a different aspect.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
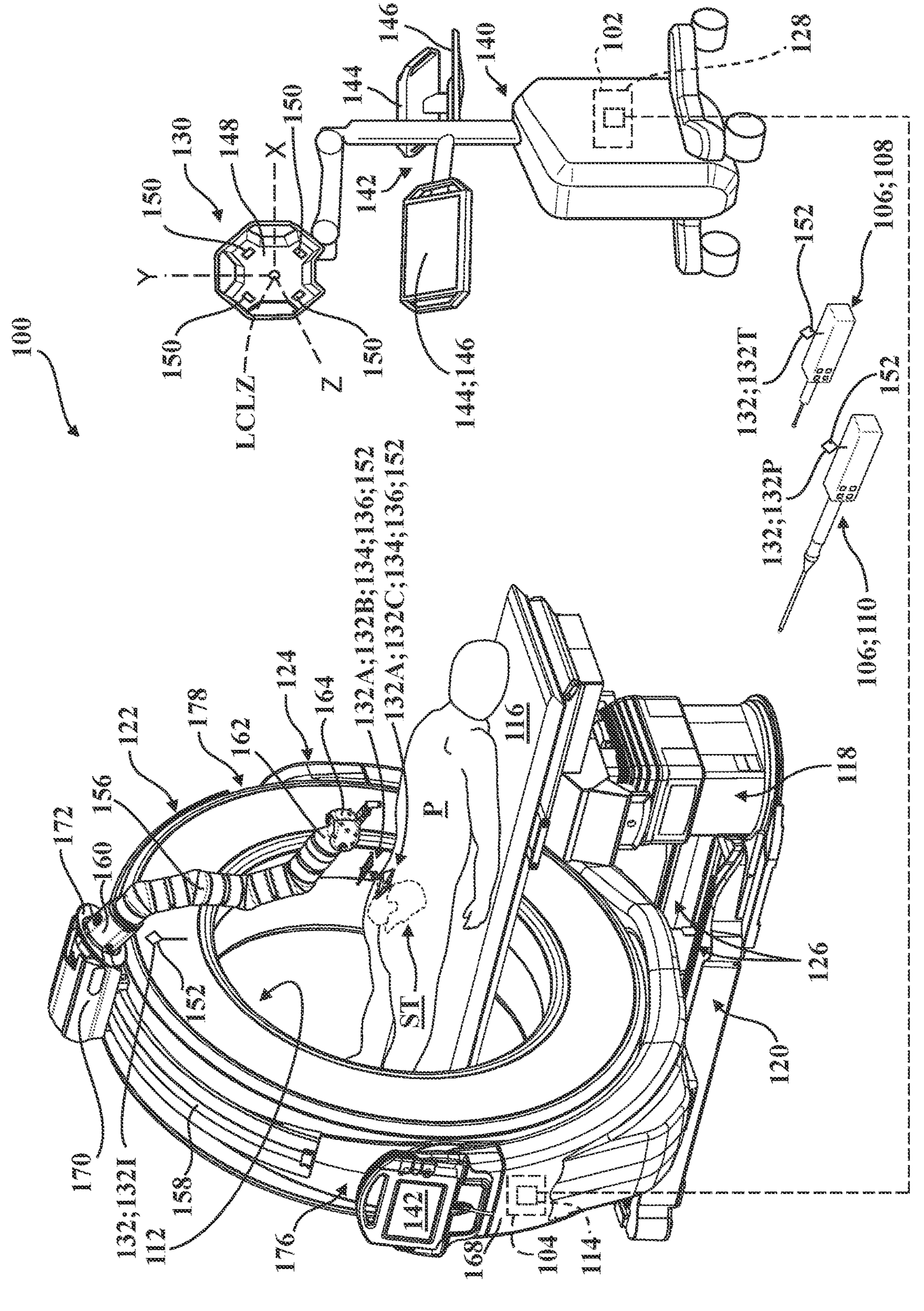
FIG. 1 is a perspective view of the surgical system, including a navigation system including a localizer to track states of trackers within a field of view, a patient tracker adapted for attachment relative to a target site, and a robotic arm configured to maintain alignment of a tool relative to the target site.

Referring now to the drawings, wherein like numerals indicate like or corresponding parts throughout the several views, a surgical system 100 is shown in FIG. 1 for treating a patient P. To this end, the illustrated surgical system 100 generally includes a navigation system 102, an imaging system 104, and one or more types of tools 106. As will be appreciated from the subsequent description below, the surgical system 100 is configured to, among other things, allow the surgeon to visualize, approach, and treat or otherwise manipulate anatomy of a patient P at a target site ST with a high level of control. To this end, imaging data ID of the target site ST may be acquired via the imaging system 104, and can be used to assist the surgeon in visualizing the patient's P anatomy at or otherwise adjacent to the target site ST. Here, the imaging data ID may also be utilized by the navigation system 102 to, among other things, facilitate navigation of tools 106 relative to the target site ST. Each of the components of the surgical system 100 introduced above will be described in greater detail below.

In FIG. 1, an operating room is shown with a patient P undergoing an exemplary surgical procedure performed using the surgical system 100. In this illustrative example, a minimally-invasive spinal surgical procedure, such as a posterior interbody spinal fusion, is being performed. It will be appreciated that this example is illustrative, and that other types of surgical procedures are contemplated. During the surgical procedure, one or more hand-held tools 106, such as a rotary tool 108 and/or a pointer tool 110, may be used by the surgeon. The tool 106 is for engaging the target site ST. As noted above and as is described in greater detail below, the navigation system 102 may be configured to track states of one or more of the tools 106 relative to the target site ST. In this exemplary surgical procedure, the rotary tool 108 may be employed as a cutting or drilling tool to remove tissue, form pilot holes (e.g., in the ilium, in vertebrae, and the like), or otherwise approach the target site ST. The rotary tool 108 may also be used to drive or otherwise install implantable components (e.g., pedicle screws, anchors, and the like).

For illustrative purposes, generically-depicted tools 106 configured for hand-held use are shown in FIG. 1. However, as will be appreciated from the subsequent description below, aspects of the surgical system 100 may be used with any suitable type of tool 106 without departing from the scope of the present disclosure. Furthermore, in addition to hand-held tools 106 of various types and configurations, aspects of the surgical system 100 may also be employed in connection with robotically-controlled tools 106 (not shown). Certain types of robotically-controlled tools 106 are disclosed in U.S. Pat. No. 9,119,655, entitled "Surgical Robotic arm Capable of Controlling a Surgical Instrument in Multiple Modes"; U.S. Pat. No. 10,456,207, entitled "Systems and Tools for use with Surgical Robotic Manipulators"; U.S. Pat. No. 11,160,620, entitled "End Effectors And Methods For Driving Tools Guided By Surgical Robotic Systems"; U.S. Pat. No. 10,959,783, entitled "Integrated Medical Imaging and Surgical Robotic System"; and U.S. Patent Application Publication No. 2020/0078097, entitled "Methods and Systems for Robot-Assisted Surgery", the disclosures of each of which are hereby incorporated by reference in their entirety.

As noted above, the imaging system 104 may be used to obtain imaging tata ID of the patient, which may be a human or animal patient. In the representative version illustrated in FIG. 1, the imaging system 104 is realized as an x-ray computed tomography (CT) imaging device. Here, the patient P may be positioned within a central bore 112 of the imaging system 104 and an x-ray source and detector may be rotated around the central bore 112 to obtain raw x-ray imaging data ID of the patient P. The imaging data ID may be processed using an imaging system controller 114, or another suitable controller, in order to construct three-dimensional imaging data ID, two-dimensional imaging data ID, and the like, which may be transmitted to or otherwise utilized by the navigation system 102 or other components of the surgical system 100.

In some versions, imaging data ID may be obtained preoperatively (e.g., prior to performing a surgical procedure) or intraoperatively (e.g., during a surgical procedure) by positioning the patient P within the central bore 112 of the imaging system 104. In order to obtain imaging data ID, a portion of the imaging system 104 may be moved relative to a patient support 116 (e.g., a surgical table) on which the patient P is disposed while the patient P remains stationary. Here, the patient support 116 is secured to the imaging system 104, such as via a column 118 which is mounted to a base 120 of the imaging system 104. A portion of the imaging system 104 (e.g., an O-shaped imaging gantry 122) which includes at least one imaging component may be supported by an articulable support 124 that can translate along the length of the base 120 on rails 126 to perform an imaging scan of the patient P, and may translate away from the patient P to an out-of-the-way position for performing a surgical procedure on the patient P.

An exemplary imaging system 104 that may be used in various versions is the AIRO® intra-operative CT system manufactured by Mobius Imaging, LLC. Examples of x-ray CT imaging devices that may be used according to various versions of the present disclosure are described in U.S. Pat. No. 10,151,810, entitled "Pivoting Multi-directional X-ray Imaging System with a Pair of Diametrically Opposite Vertical Support Columns Tandemly Movable Along a Stationary Base Support"; U.S. Pat. No. 9,962,132, entitled "Multi-directional X-ray Imaging System with Single Support Column"; U.S. Pat. No. 9,801,592, entitled "Caster System for Mobile Apparatus"; U.S. Pat. No. 9,111,379, entitled "Method and System for X-ray CT Imaging"; U.S. Pat. No. 8,118,488, entitled "Mobile Medical Imaging System and Methods"; and U.S. Patent Application Publication No. 2014/0275953, entitled "Mobile X-ray Imaging System", the disclosures of each of which are hereby incorporated by reference in their entirety.

While the illustrated imaging system 104 is realized as an x-ray CT imaging device as noted above, in other versions, the imaging system 104 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. Other configurations are contemplated. In some versions, the imaging system 104 may be a mobile CT device that is not attached to the patient support 116 and may be wheeled or otherwise moved over the patient P and the patient support 116 to perform a scan. Examples of mobile CT devices include the BodyTom® CT scanner from Samsung Electronics Co., Ltd. and the O-Arm® surgical imaging system form Medtronic, plc. The imaging system 104 may also be a C-arm x-ray fluoroscopy device. In other versions, the imaging system 104 may be a fixed-bore imaging device, and the patient P may be moved into the bore of the device, either on a patient support 116 or on a separate patient table that is configured to slide in and out of the central bore 112. Further, although the imaging system 104 shown in FIG. 1 is located close to the patient P within the operating room, the imaging system 104 may be located remotely, such as in another room or building (e.g., in a hospital radiology department).

The surgical system 100 employs the navigation system 102 to, among other things, track movement of various objects, such as the tools 106 and parts of the patient's P anatomy (e.g., tissue at the target site ST), as well as portions of the imaging system 104 in some versions. To this end, the navigation system 102 comprises a navigation controller 128 coupled to a localizer 130 that is configured to sense the position and/or orientation of trackers 132 within a localizer coordinate system LCLZ. In other words, the navigation system 102 includes the localizer 130 to track states of trackers 132 within a field of view. As is described in greater detail below, the trackers 132 (also referred to herein as "navigable trackers") are fixed, secured, or otherwise attached to specific objects, and are configured to be monitored by the localizer 130.

The navigation controller 128 is disposed in communication with the localizer 130 and gathers position and/or orientation data for each tracker 132 sensed by the localizer 130 in the localizer coordinate system LCLZ. The navigation controller 128 may be disposed in communication with the imaging system controller 114 (e.g., to receive imaging data ID) and/or in communication with other components of the surgical system 100 (e.g., robotic arm controllers, tool controllers, and the like; not shown). However, other configurations are contemplated. The controllers 114, 128 may be realized as computers, processors, control units, and the like, and may be discrete components, may be integrated, and/or may otherwise share hardware.

It will be appreciated that the localizer 130 can sense the position and/or orientation of multiple trackers 132 to track correspondingly multiple objects within the localizer coordinate system LCLZ. By way of example, and as is depicted in FIG. 1, trackers 132 may comprise a tool tracker 132T, a pointer tracker 132P, an imaging system tracker 1321, one or more patient trackers 132A (e.g., a first patient tracker 132A, a second patient tracker 132B, and the like), a robot tracker 132R, as well as additional patient trackers, trackers for additional medical and/or surgical tools, and the like. The patient tracker 132A is adapted for attachment relative to the target site ST.

Figure 2:
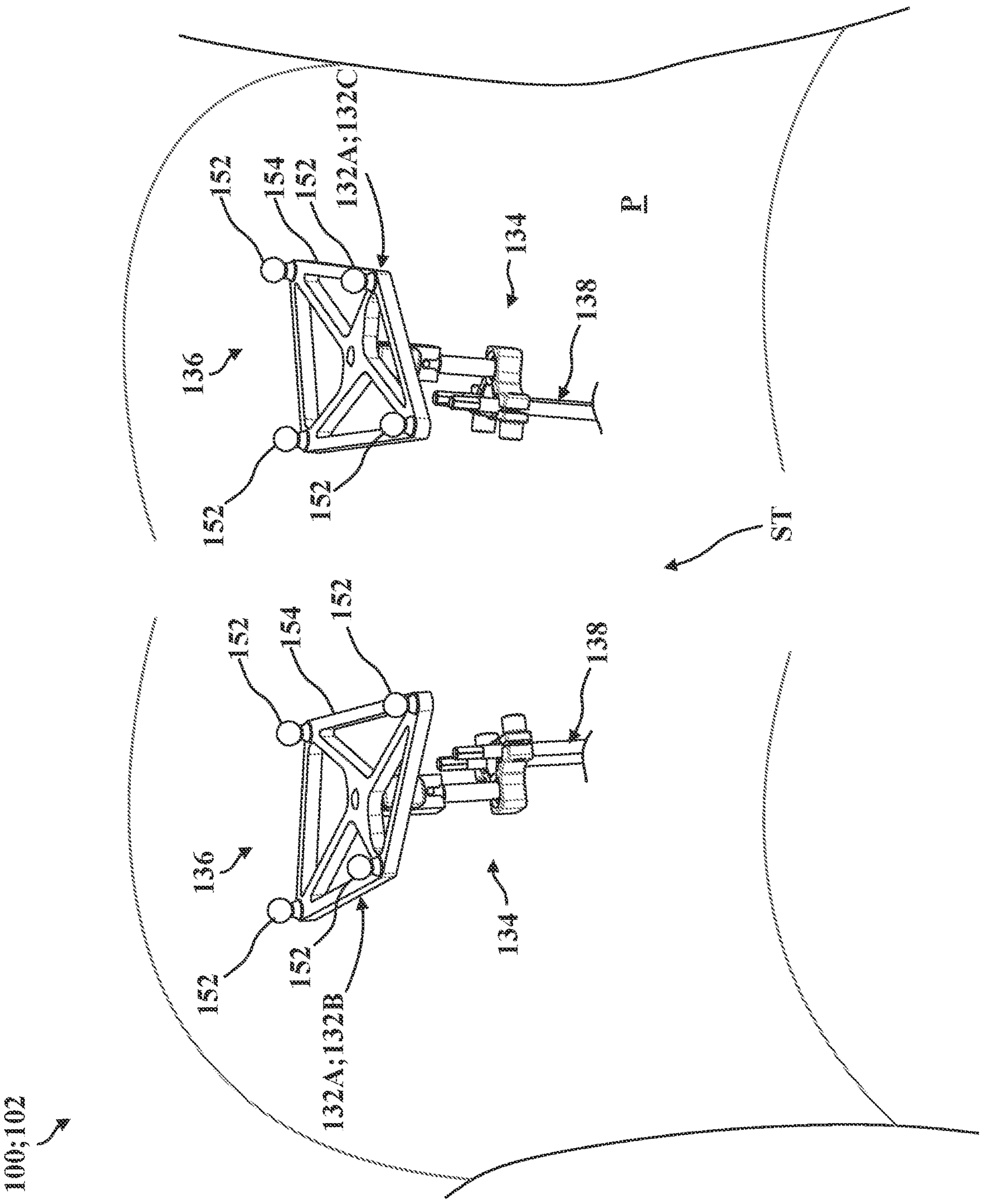
FIG. 2 is a perspective view of the patient tracker attached relative to the target site.
Figure 3:
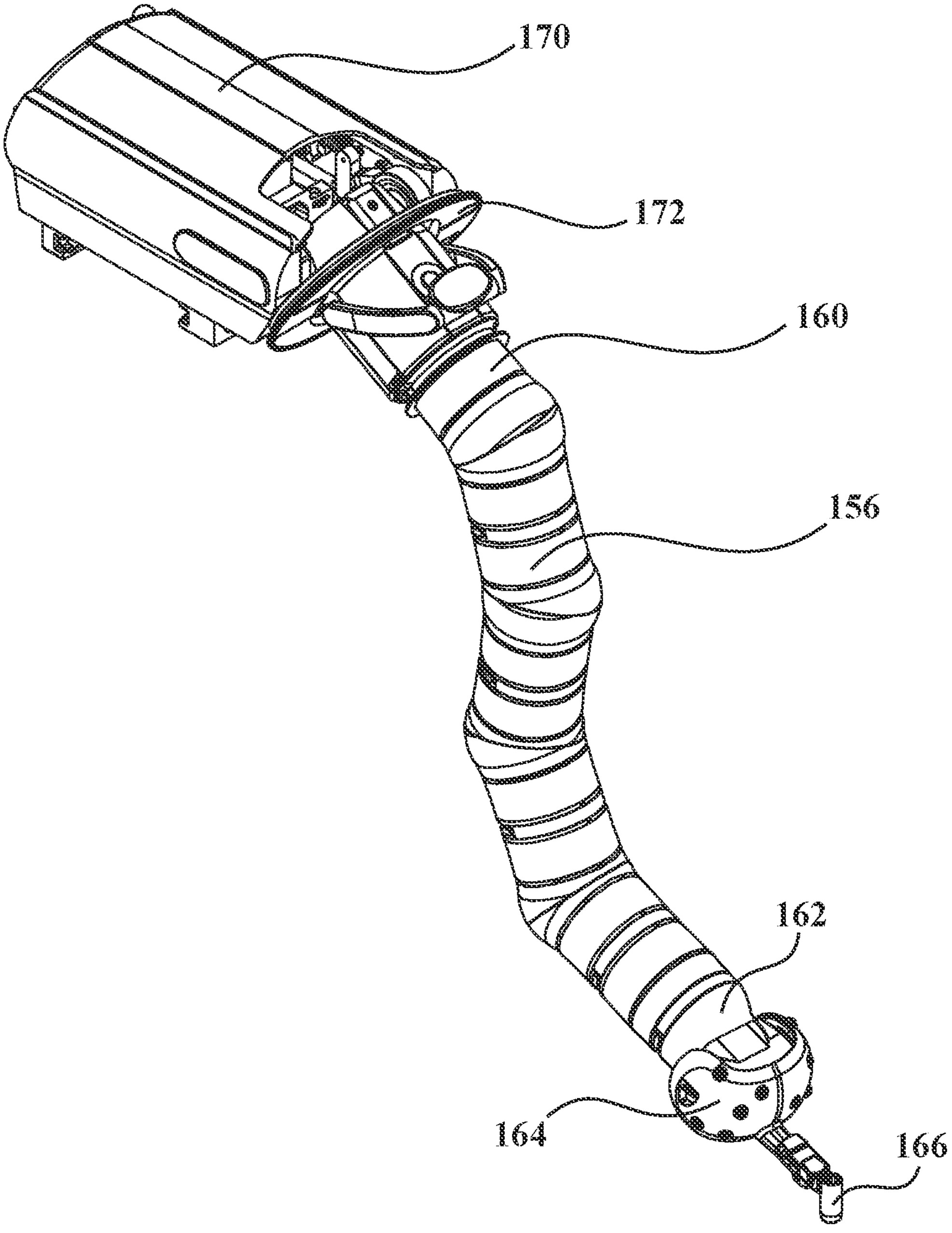
FIG. 3 is a perspective view of the robotic arm of FIG. 1, with the robotic arm extending between a base end and a mount end arranged for movement relative to the base end, with an end effector coupled to the mount end of the robotic arm.

In FIG. 1, the tool tracker 132T, the pointer tracker 132P, and the imaging system tracker 1321 are each depicted generically and are shown firmly fixed to (or otherwise integrated with) the rotary tool 108, the pointer tool 110, and the gantry 122 of the imaging system 104, respectively. The first and second patient trackers 132A, 132B, on the other hand, are removably coupled to mount assemblies 134 to define tracker assemblies 136 which facilitate selective movement of the trackers 132A, 132B relative to their mount assemblies 134 according to versions of the present disclosure, as described in greater detail below. As shown in FIG. 2, the tracker assemblies 136 are firmly fixed to different portions of the patient's P anatomy (e.g., to opposing lateral sides of the ilium) via anchors 138 which are configured to releasably engage tissue (e.g., bone). It will be appreciated that trackers 132 may be firmly affixed to different types of tracked objects (e.g., discrete bones, tools, pointers, and the like) in a number of different ways.

The position of the patient trackers 132A, 132B relative to the anatomy of the patient P to which they are attached can be determined by known registration techniques, such as point-based registration in which the pointer tool 110 (to which the pointer tracker 132P is fixed) is used to touch off on bony landmarks on bone, or to touch off on several points across the bone for surface-based registration. Conventional registration techniques can be employed to correlate the pose of the patient trackers 132A, 132B to the patient's anatomy. Other types of registration are also possible.

Position and/or orientation data may be gathered, determined, or otherwise handled by the navigation controller 128 using conventional registration/navigation techniques to determine coordinates of trackers 132 within the localizer coordinate system LCLZ. These coordinates may be utilized by various components of the surgical system 100 (e.g., to facilitate control of the tools 106, to facilitate navigation based on imaging data ID, and the like).

In the representative version illustrated in FIG. 1, the navigation controller 128 and the localizer 130 are supported on a mobile cart 140 which is movable relative to the base 120 of the imaging system 104. The mobile cart 140 also supports a user interface, generally indicated at 142, to facilitate operation of the navigation system 102 by displaying information to, and/or by receiving information from, the surgeon or another user. The user interface 142 may be disposed in communication with other components of the surgical system 100 (e.g., with the imaging system 104), and may comprise one or more output devices 144 (e.g., monitors, indicators, display screens, and the like) to present information to the surgeon (e.g., images, video, data, a graphics, navigable menus, and the like), and one or more input devices 146 (e.g., buttons, touch screens, keyboards, mice, gesture or voice-based input devices, and the like).

In some versions, the surgical system 100 is capable of displaying a virtual representation of the relative positions and orientations of tracked objects to the surgeon or other users of the surgical system 100, such as with images and/or graphical representations of the anatomy of the patient P and the tool 106 presented on one or more output devices 144 (e.g., a display screen). The navigation controller 128 may also utilize the user interface 142 to display instructions or request information from the surgeon or other users of the surgical system 100. Other configurations are contemplated. One type of mobile cart 140 and user interface 142 of this type of navigation system 102 is described in U.S. Pat. No. 7,725,162, entitled "Surgery System", the disclosure of which is hereby incorporated by reference in its entirety.

Because the mobile cart 140 and the gantry 122 of the imaging system 104 can be positioned relative to each other and also relative to the patient P in the representative version illustrated in FIG. 1, the navigation system 102 can transform the coordinates of each tracker 132 from the localizer coordinate system LCLZ into other coordinate systems (e.g., defined by different trackers 132, localizers 130, and the like), or vice versa, so that navigation relative to the target site ST (or control of tools 106) can be based at least partially on the relative positions and orientations of multiple trackers 132 within a common coordinate system (e.g., the localizer coordinate system LCLZ). Coordinates can be transformed using a number of different conventional coordinate system transformation techniques. It will be appreciated that the localizer 130 or other components of the navigation system 102 could be arranged, supported, or otherwise configured in other ways without departing from the scope of the present disclosure. By way of non-limiting example, the localizer 130 could be coupled to the imaging system 104 in some versions (e.g., to the gantry 122). Other configurations are contemplated.

In the illustrated version, the localizer 130 is an optical localizer and includes a camera unit 148 with one or more optical position sensors 150. The navigation system 102 employs the optical position sensors 150 of the camera unit 148 to sense the position and/or orientation of the trackers 132 within the localizer coordinate system LCLZ. To this end, the trackers 132 each employ one or more markers 152 (also referred to as "fiducials" in some versions) that are supported on an array 154 in a predetermined arrangement. However, as will be appreciated from the subsequent description below, trackers 132 may have different configurations, such as with different quantities of markers 152 that can be secured to or otherwise formed in other structures besides the arrays 154 illustrated throughout the drawings (e.g., various types of housings, frames, surfaces, and the like). Other configurations are contemplated.

In some versions, certain trackers 132 (e.g., the patient tracker 132A) may employ "passive" markers 152 (e.g., reflective markers such as spheres, cones, and the like) which reflect emitted light that is sensed by the optical position sensors 150 of the camera unit 148. In some versions, trackers 132 employ "active" markers 152 (e.g., light emitting diodes "LEDs"), which emit light that is sensed by the optical position sensors 150 of the camera unit 148. Examples of navigation systems 102 of these types are described in U.S. Pat. No. 9,008,757, entitled "Navigation System Including Optical and Non-Optical Sensors", the disclosure of which is hereby incorporated by reference in its entirety.

Although one version of the mobile cart 140 and localizer 130 of the navigation system 102 is illustrated in FIG. 1, it will be appreciated that the navigation system 102 may have any other suitable configuration for monitoring trackers 132 which, as will be appreciated from the subsequent description below, may be of various types and configurations and could employ various types of markers 152. Thus, for the purposes of clarity and consistency, the term "marker 152" is used herein to refer to a portion of a tracker 132 (e.g., a passive or active marker 152 mounted to an array 154 or otherwise coupled to a tracked object) that can be monitored by a localizer 130 to track (e.g., states, motion, position, orientation, and the like) of the object to which the tracker 132 is secured, irrespective of the specific type or configuration of the localizer 130 and/or tracker 132.

In some versions, the navigation system 102 and/or the localizer 130 could be radio frequency (RF) based. For example, the navigation system 102 may comprise an RF transceiver coupled to the navigation controller 128. Here, certain trackers 132 may comprise markers 152 realized as RF emitters or transponders, which may be passive or may be actively energized. The RF transceiver transmits an RF tracking signal, and the RF emitters respond with RF signals such that tracked states are communicated to (or interpreted by) the navigation controller 128. The RF signals may be of any suitable frequency. The RF transceiver may be positioned at any suitable location to track the objects using RF signals effectively. Furthermore, it will be appreciated that versions of RF-based navigation systems may have structural configurations that are different than the navigation system 102 illustrated throughout the drawings.

In some versions, the navigation system 102 and/or localizer 130 may be electromagnetically (EM) based. For example, the navigation system 102 may comprise an EM transceiver coupled to the navigation controller 128. Here, certain trackers 132 may comprise markers 152 realized as EM components (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 128. The navigation controller 128 may analyze the received EM signals to associate relative states thereto. Here too, it will be appreciated that versions of EM-based navigation systems may have structural configurations that are different than the navigation system 102 illustrated throughout the drawings.

Those having ordinary skill in the art will appreciate that the navigation system 102 and/or localizer 130 may have any other suitable components or structure not specifically recited herein. Furthermore, any of the techniques, methods, and/or components described above with respect to the camera-based navigation system 102 shown throughout the drawings may be implemented or provided for any of the other versions of the navigation system 102 described herein. For example, the navigation system 102 may also be based on one or more of inertial tracking, ultrasonic tracking, image-based optical tracking (e.g., with markers 152 are defined by patterns, shapes, edges, and the like that can be monitored with a camera), or any combination of tracking techniques. Other configurations are contemplated.

As shown in FIG. 1, the surgical system 100 may include a robotic arm 156 operatively attached to a support element 158 and configured to maintain alignment of the tool 106 relative to the target site ST. The robotic arm 156 may extend between a base end 160 and a mount end 162 arranged for movement relative to the base end 160. The surgical system 100 may further includes an end effector 164 attached to the mount end 162 of the robotic arm 156 and configured to support one or more types of tools 106, instruments, and the like. More specifically, the surgical system 100 may further include a tool guide 166 supported by the end effector 164, and the tool guide 166 may be configured to support the tool 106 relative to a trajectory that is aligned or otherwise determined relative to the target site ST on the patient P.

The robotic arm 156 may comprise a multi-joint arm that includes a plurality of linkages connected by joints having actuator(s) and optional encoder(s) (not shown in detail) to enable the linkages to bend, rotate and/or translate relative to one another in response to control signals from a robot control system. The robotic arm 156 may be fixed to the imaging system 104, such as on the support element 158 (e.g. a curved rail) that may extend concentrically over the outer surface of the O-shaped imaging gantry 122 of the imaging system 104 and that may be located close to the target site ST of the patient P. In some versions, the robotic arm 156 could be coupled to a mobile cart (not shown) or to another type of support element 158 that is not necessarily coupled to the imaging system 104. Although a single robotic arm 156 is shown in FIG. 1, it will be understood that the surgical system 100 may include multiple robotic arms attached to suitable support structure(s). Other configurations are contemplated.

The support element 158 may form a semicircular arc and may be concentric with the outer circumference of the O-shaped imaging gantry 122. The support element 158 may extend around at least 25%, such as between about 30-50% of the outer circumference of the O-shaped imaging gantry 122. The support element 158 may extend around at least a portion of the outer circumference of the O-shaped imaging gantry 122 that is located above the target site ST of the patient P. More specifically, the base end 160 of the robotic arm 156 (e.g., the end of the robotic arm 156 opposite the end effector 164) may be fixed to the support element 158, in a non-limiting example, at a position that is less than about 2 meters, such as less than about 1 meter (e.g., between and 1 meter) from the target site ST of the patient P during a surgical procedure.

In versions, the support element 158 may extend along a semicircular arc having a radius that is greater than about 33 inches, such as greater than about 35 inches (e.g., between 33 and 50 inches). The support element 158 may be spaced from the outer surface of the O-shaped imaging gantry 122 by a pre-determined distance, which may be from less than an inch (e.g., 0.5 inches) to 6 or 10 inches or more. In some versions, the support element 158 may be spaced from the O-shaped imaging gantry 122 by an amount sufficient to enable the tilt motion of the O-shaped imaging gantry 122 with respect to a gimbal 168 supporting the O-shaped imaging gantry 122 over at least a limited range of motion. Additionally, in some versions, the support element 158 may comprise one or more straight segments (e.g., rail segments), where at least a portion of the support element 158 may extend over the top surface of the O-shaped imaging gantry 122. Other configurations are contemplated.

A carriage 170 may be located on the support element 158 and may include a mounting surface 172 for mounting the base end 160 of the robotic arm 156 to the carriage 170. As shown in FIG. 1, the carriage 170 may extend from the support element 158 towards a first (e.g., front) face of the O-shaped imaging gantry 122. The mounting surface 172 for the robotic arm 156 may extend beyond the first (e.g., front) face of the O-shaped imaging gantry 122 and the robotic arm 156 may extend over the first (e.g., front) face of the O-shaped imaging gantry 122. In some versions, the configuration of the carriage 170 and the mounting surface 172 may be reversed such that the mounting surface 172 extends beyond the second (e.g., rear) face of the O-shaped imaging gantry 122, and the robotic arm 156 may extend over the second (e.g., rear) face of the O-shaped imaging gantry 122. In this configuration, the patient support 116 may be configured such that the patient support 116 and patient P extend into or through the central bore 112 defined through the O-shaped imaging gantry 122, and a portion of the patient P requiring surgical intervention (e.g., the cranium) may be accessed from the second (e.g., rear) side of the imaging gantry 122.

In some versions, the carriage 170 and the robotic arm 156 attached thereto may be moved to different positions along the length of support element 158 (e.g., any arbitrary position between a first end 176 and a second end 178 of the support element 158). The carriage 170 and the robotic arm 156 may be fixed in place at a particular desired position along the length of the support element 158. In some versions, the carriage 170 may be moved manually (e.g., positioned by an operator at a particular location along the length of the support element 158 and then clamped or otherwise fastened in place). Alternately, the carriage 170 may be driven to different positions using a suitable drive mechanism (e.g., a motorized belt drive, friction wheel, gear tooth assembly, cable-pulley system, etc., not shown in detail). The drive mechanism may be located on the carriage 170 and/or the support element 158, for example. An encoder mechanism may be utilized to indicate the position of the carriage 170 and the base end 160 of the robotic arm 156 on the support element 158. Although the version of FIG. 1 illustrates one robotic arm 156 mounted to the support element 158, it will be understood that more than one robotic arm 156 may be mounted to the support element 158 via respective carriages 170.

In some versions, the robotic arm 156 may be mounted directly to the support element 158, such as on a mounting surface 172 that is integrally formed on the support element 158. In such an version, the position of robotic arm 156 may not be movable along the length of the support element 158.

In other versions, the robotic arm 156 may be secured to any other portion of the imaging system 104, such as directly mounted to the gantry 122. Alternatively, the robotic arm 156 may be mounted to the patient support 116 or column 118, to any of the wall, ceiling or floor in the operating room, or to a separate cart as noted above. In some versions, the robotic arm 156 may be mounted to a separate mobile shuttle, similar to as is described in U.S. Pat. No. 11,103, 990, entitled "System and Method for Mounting a Robotic Arm in a Surgical Robotic System", the disclosure of which is hereby incorporated by reference in its entirety. Although a single robotic arm 156 is shown in FIG. 1, it will be understood that two or more robotic arms 156 may be utilized.

Those having ordinary skill in the art will appreciate that the robotic arm 156 can be employed to aid in the performance of various types of surgical procedures, such as a minimally-invasive spinal surgical procedure or various other types of orthopedic, neurological, cardiothoracic and general surgical procedures. In the version of FIGS. 1 and 2, the robotic arm 156 may be used to assist a surgeon performing a surgical procedure in the lumbar spinal region of a patient. The robotic arm 156 may also be used for thoracic and/or cervical spinal procedures. The procedures may be performed posteriorly, anteriorly or laterally. Other configurations are contemplated.

In some versions, the robotic arm 156 may be controlled to move the end effector 164 to one or more pre-determined positions and/or orientations with respect to a patient P, such as to and/or along a trajectory defined relative to the anatomy of the patient P. As discussed above, the end effector 164 may be realized as or may otherwise support various types of instruments and/or tools 106 including, but not limited to, a needle, a cannula, a dilator, a cutting or gripping instrument, a scalpel, a drill, a screw, a screwdriver, an electrode, an endoscope, an implant, a radiation source, a drug, etc., that may be inserted into the body of the patient P. In some versions, the end effector 164 may be realized as a hollow tube or cannula configured to receive a surgical tool 106, including without limitation a needle, a cannula, a dilator, a cutting or gripping instrument, a scalpel, a drill, a screw, a screwdriver, an electrode, an endoscope, an implant, a radiation source, a drug, and the like. The surgical tool 106 may be inserted into or otherwise adjacent to the patient's body through the hollow tube or cannula by a surgeon. The robotic arm 156 may be controlled to maintain the position and orientation of the end effector 164 with respect to the patient P to ensure that the surgical tool(s) 106 follow a desired trajectory through the patient's body to reach the target site ST. The target site ST may be determined preoperatively and/or intraoperatively, such as during a surgical planning process, based on patient images which may be obtained using the imaging system 104.

In the representative version illustrated herein, the navigation system 102 tracks the robotic arm 156 within the localizer coordinate system LCLZ via the robot tracker 132R, as is described in greater detail below. To this end, a control loop may continuously read the tracking data and current parameters (e.g., joint parameters) of the robotic arm 156, and may send instructions to the navigation controller 128 and/or to the imaging system controller 114 (and/or some other controller, such as a robot controller) to cause the robotic arm 156 to move to a desired position and orientation within the localizer coordinate system LCLZ.

In some versions, a surgeon may use one or more portions of the surgical system 100 as a planning tool for a surgical procedure, such as by setting trajectories within the patient for inserting tools 106, as well as by selecting one or more target sites ST for a surgical intervention within the patient's body. The trajectories and/or target sites ST set by the surgeon may be saved (e.g., in a memory of a computer device) for later use during surgery. In some versions, the surgeon may be able to select stored trajectories and/or target sites ST using the surgical system 100, and the robotic arm 156 may be controlled to perform a particular movement based on the selected trajectory and/or target site ST. For example, the robotic arm 156 may be moved to position the end effector 164 of the robotic arm 156 into alignment with the pre-defined trajectory and/or over the pre-determined target site ST. As discussed above, the end effector 164 may include the tool guide 166 which may be used to guide the tool 106 relative to the patient's body along the pre-defined trajectory and/or to the pre-defined target site ST.

As discussed above, the localizer 130 may include a camera unit 148 with one or more optical position sensors 150. More specifically, the optical position sensors 150 may be light sensors capable of sensing changes in infrared (IR) emitted within a field of view. In some versions, the localizer 130 may include one or more radiation sources (e.g., one or more diode rings) that direct radiation (e.g., IR radiation) into the surgical field, where the radiation may be reflected by the markers 152 and received by the cameras. In the illustrated version, certain active markers 152 (e.g., active markers 152 which define the robot tracker 132R) are configured to emit IR light detectable by the optical position sensors 150 of the localizer 130. The navigation controller 128 may be coupled to the localizer 130 and may determine the positions and/or orientations of markers 152 detected by the optical position sensors 150 using, for example, triangulation and/or transformation techniques. A 3D model and/or mathematical simulation of the surgical space may be generated and continually updated using motion tracking software implemented by the navigation controller 128.

Figure 4:
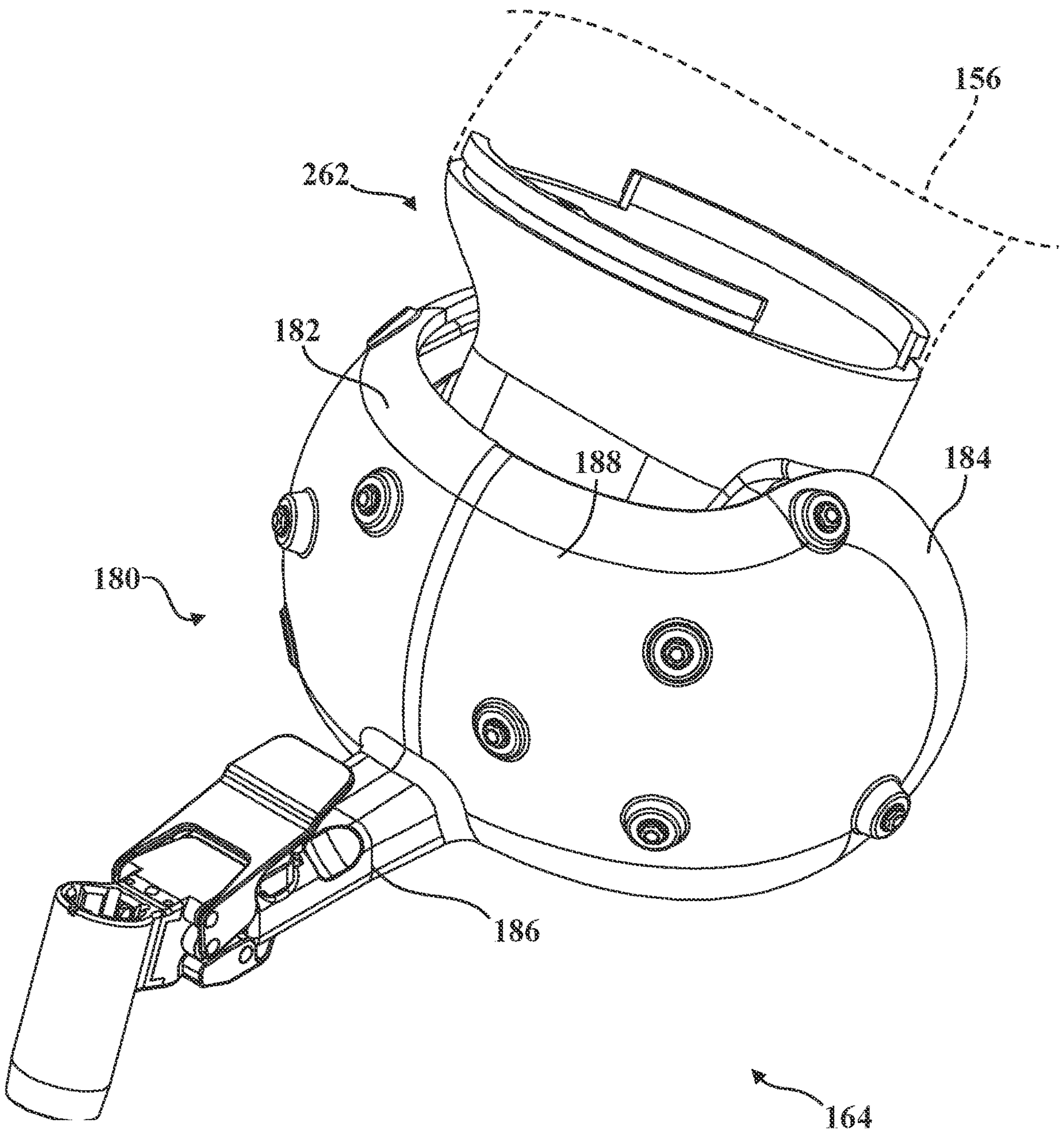
FIG. 4 is an enlarged perspective view of the end effector coupled to the mount end of the robotic arm of FIG. 3 with the robotic arm shown partially in phantom.
Figure 5:
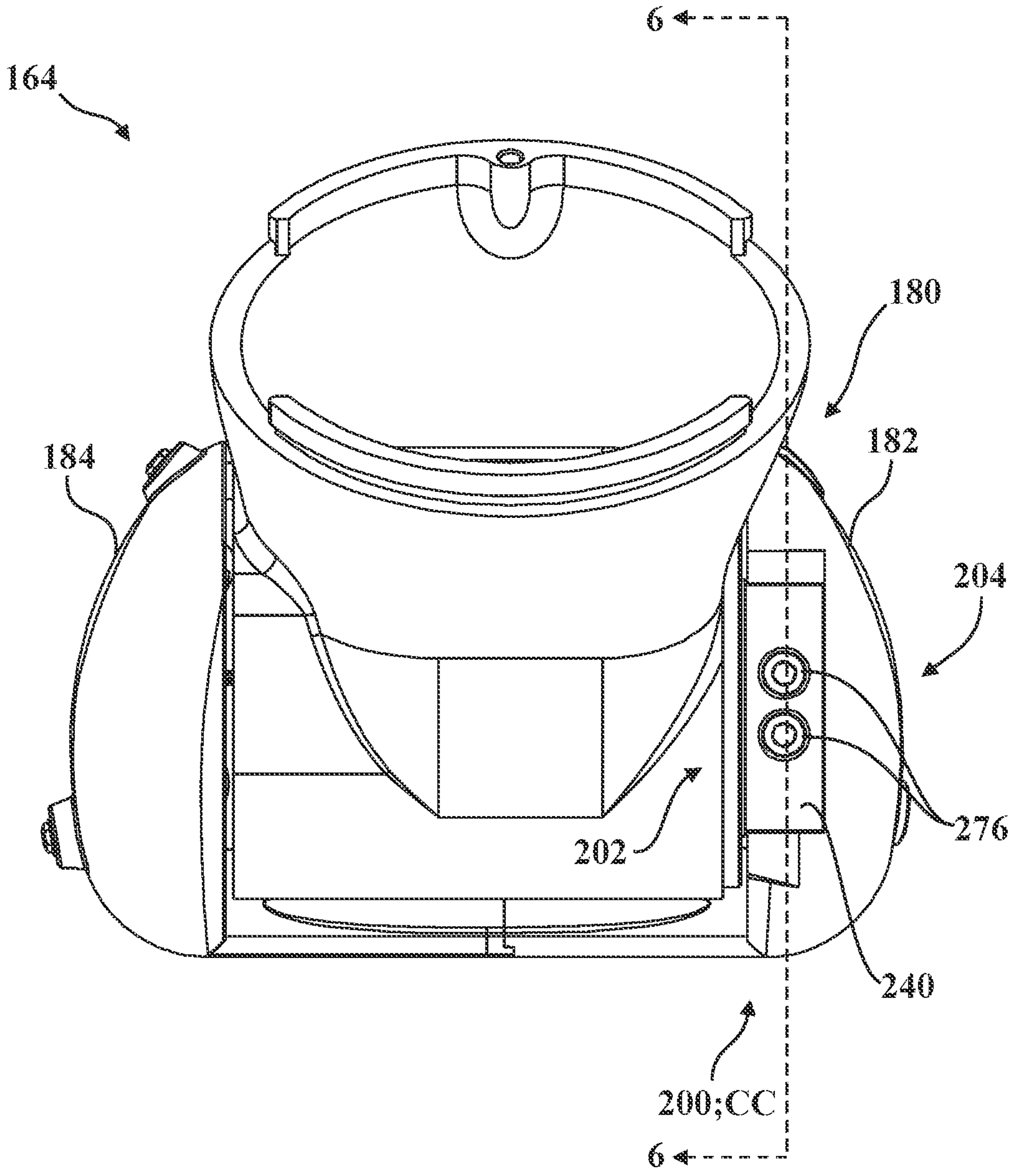
FIG. 5 is a rear side view of the mount end of the robotic arm and an end effector having a first implementation of a coupling system for removing the end effector from the robotic arm.

Turning now to FIG. 4, the mount end 162 and the end effector 164 are shown close-up, while the rest of the robotic arm 156 is illustrated in phantom. The end effector 164 comprises a body 180 having a first body portion 182 and a second body portion 184, which are coupled to each other. The end effector 164 further comprises a guide mount 186 coupled to the body 180 and protruding in a direction generally away from the mount end 162 of the robotic arm 156. As mentioned above, the end effector 164 may be attached to the robotic arm 156. More specifically and as shown here, the end effector 164 may be removably coupled to the mount end 162 of the robotic arm 156. The end effector 164 may be removed from the robotic arm 156 for a variety of reasons, such as cleaning and/or sterilization of the end effector 164, allowing the use of a different end effector (not shown) having different characteristics, maintenance or repair of the end effector 164, or upgrades, etc. Other reasons for removing the end effector 164 may include a surgeon's need to utilize, view, or otherwise access the target site ST during a procedure while a tool is in situ. Generally, the end effector 164 will be subsequently recoupled to the robotic arm 156 for further use. As will be appreciated, tracking the end effector 164 with high precision and accuracy is facilitated by a precise and repeatable connection between the end effector 164 and the robotic arm 156.

Similar to the tools 106 above, the pose of the end effector 164 can be measured and determined using the navigation system 102. Specifically, the localizer 130 is able to identify and track markers 188 that are coupled to the body 180 of the end effector 164 and, using a known geometry of the markers 188 on the body 180, determine the position and orientation of the end effector 164. Accurate and precise tracking is further facilitated by a known kinematic (i.e., positional) relationship between the end effector 164 and the robotic arm 156. The known kinematic relationship may be determined and/or verified for each new surgical procedure through a calibration process. It should be appreciated that maintaining this known kinematic relationship when the end effector 164 has been removed from the robotic arm 156 and subsequently reconnected is beneficial to accurate and precise tracking.

Shown in FIGS. 5-10, the surgical system 100 further comprises a coupling system 200 for removably attaching the end effector 164 to the mount end 162 of the robotic arm 156. The coupling system 200 comprises a first coupler portion 202 coupled to the robotic arm 156 and a second coupler portion 204 coupled to the end effector 164. The first coupler portion 202 and the second coupler portion 204 are engageable to repeatably and accurately couple the end effector 164 to the robotic arm 156. More specifically, the second coupler portion 204 is coupled to the second body portion 184 of the body 180. The coupling system 200 further comprises a clamping mechanism 206 operatively engageable between the first coupler portion 202 and the second coupler portion 204 for securing the first coupler portion 202 to the second coupler portion 204.

The clamping mechanism 206 urges the first coupler portion 202 into engagement with the second coupler portion 204 to kinematically secure the end effector 164 to the robotic arm 156. In a first implementation shown in FIGS. 5-12, the clamping mechanism 206 is mechanically coupled to the second coupler portion 204 to secure the end effector 164. A second implementation of the clamping mechanism 406 is shown in FIGS. 13-17 and is operable by a user to quickly remove the end effector 164 from, and/or reattach the end effector 164 to, the robotic arm 156.

Figure 6:
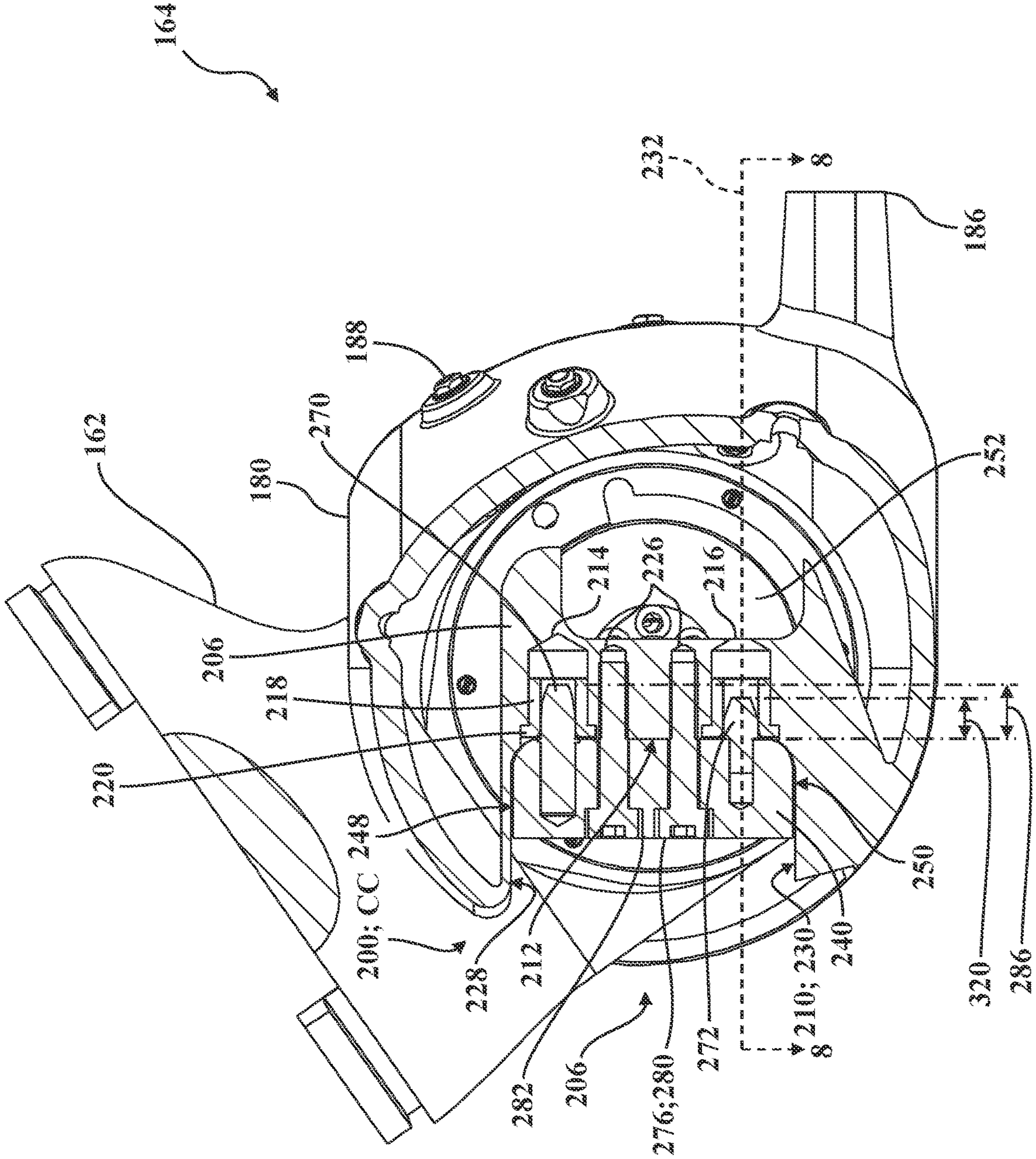
FIG. 6 is a cross-sectional view of the end effector taken along line 6-6 of FIG. 5 showing a first coupler portion and a second coupler portion of the coupling system in a clamped configuration.
Figure 7:
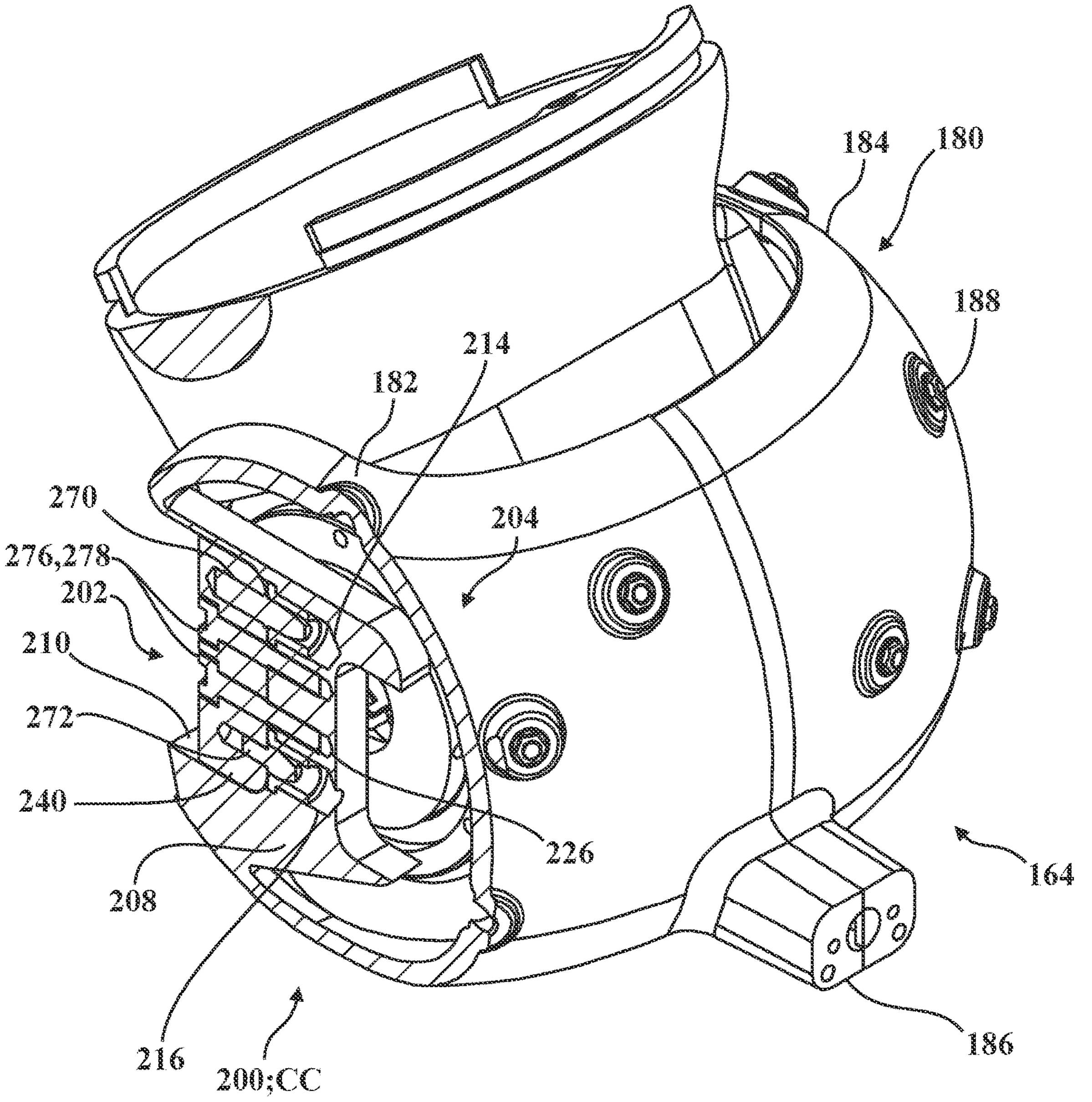
FIG. 7 is a cross-sectional perspective view of the end effector and coupling system in the clamped configuration of FIG. 6.
Figure 8:
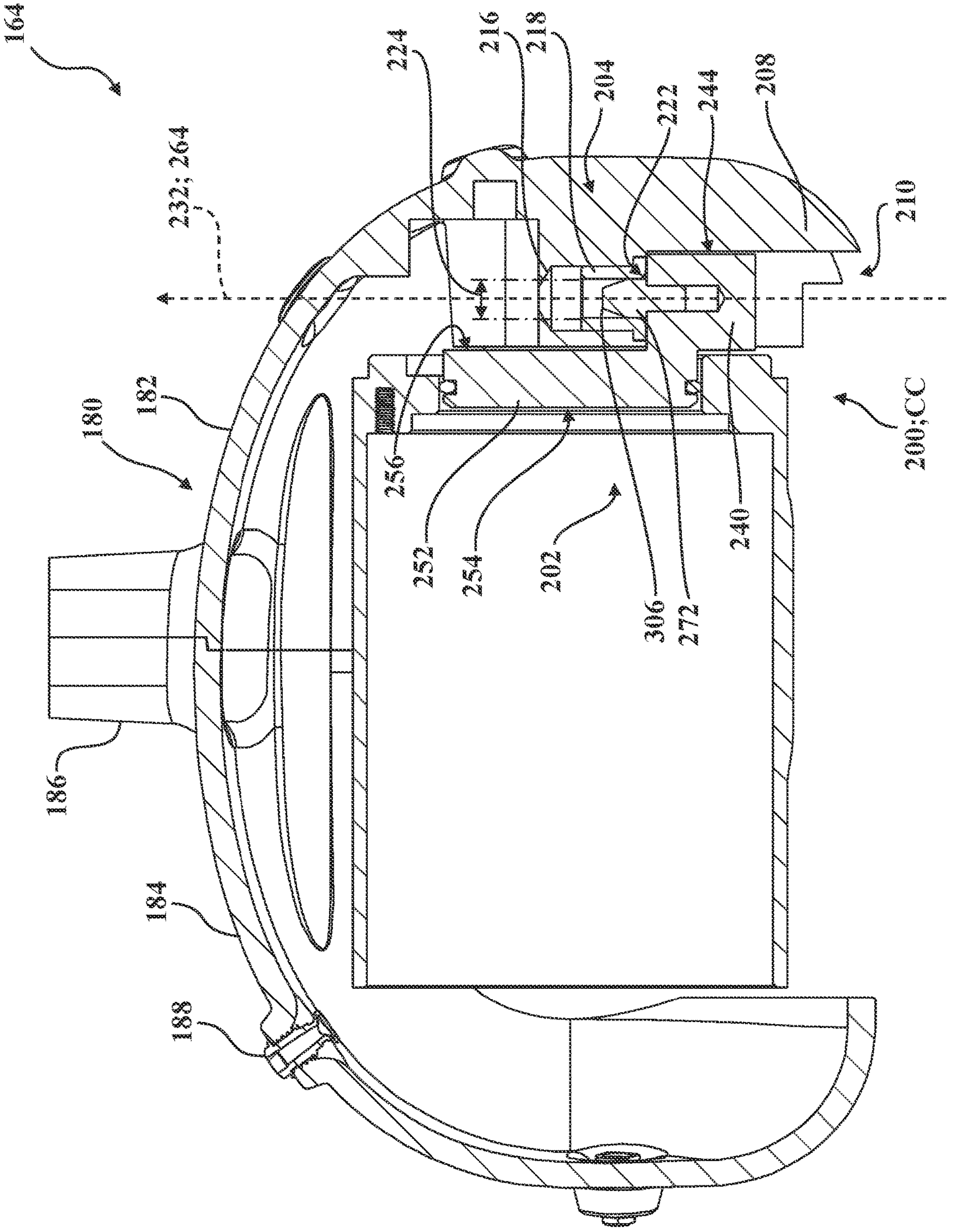
FIG. 8 is a top-side cross sectional view of the end effector taken along the line 8-8 of FIG. 7 showing an alignment pin engaged with an alignment socket.
Figure 9:
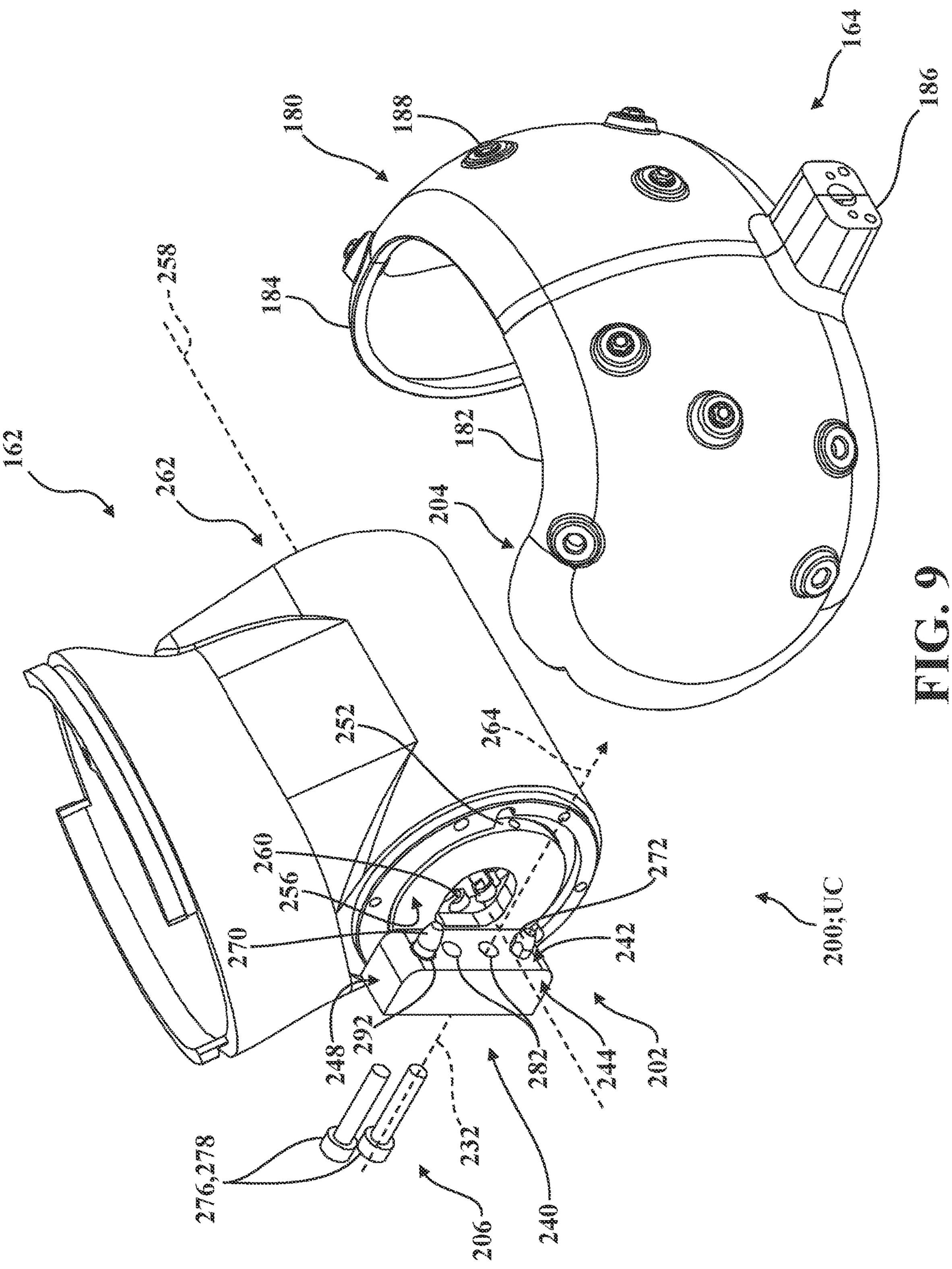
FIG. 9 is a partially exploded front-side perspective view of the mount end of the robotic arm and the end effector showing the coupling system first coupler portion, the second coupler portion, and a clamping member in an unclamped configuration.
Figure 10:
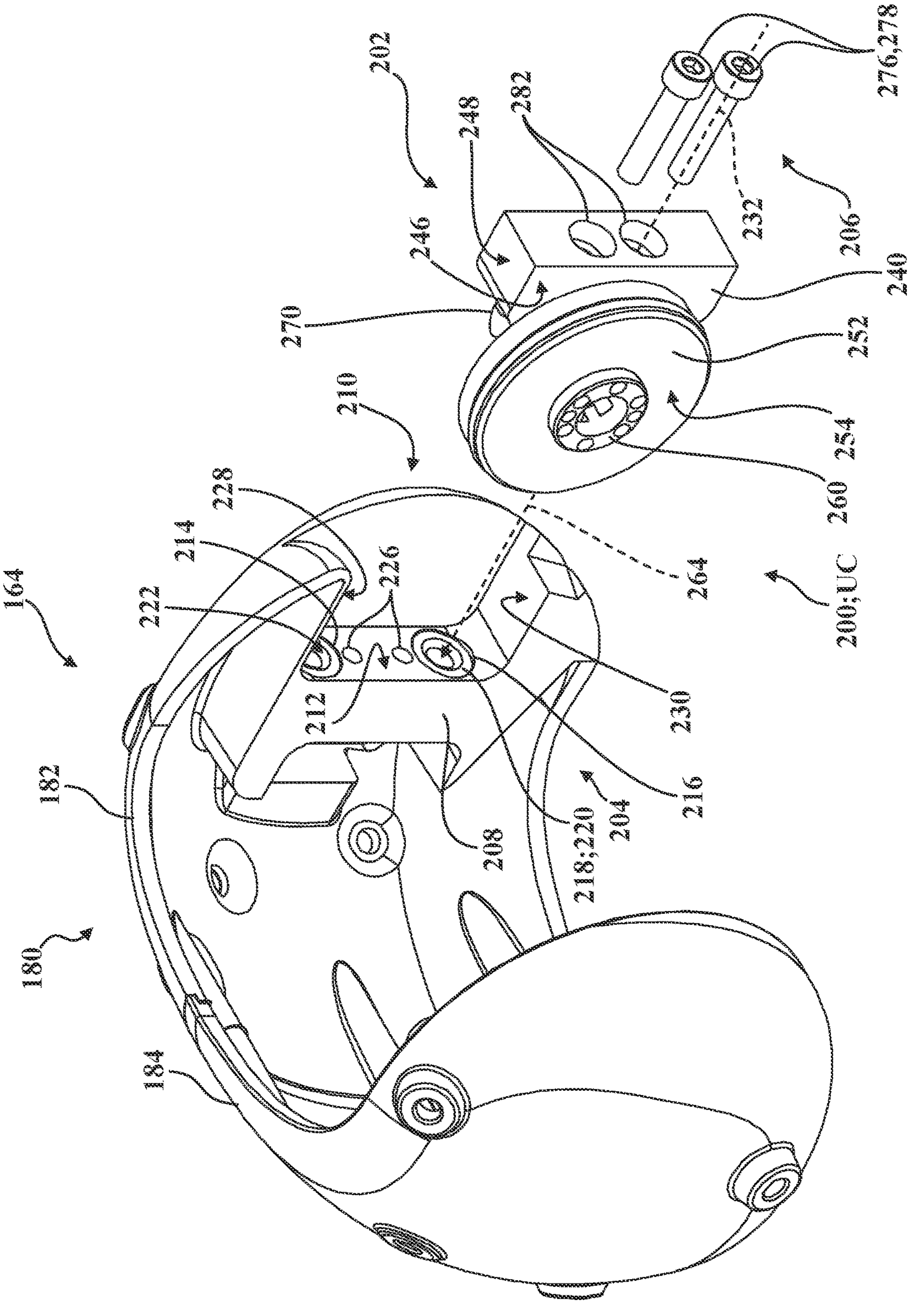
FIG. 10 is a partially exploded rear-side perspective view of the end effector, the first coupler portion, the second coupler portion, and the clamping member.

Turning now to FIGS. 6, 8, and 10, further details of the first implementation of the coupling system 200 are shown. Here, the second coupler portion 204 comprises a socket body 208, which defines a receiver 210 having a floor surface 212. The second coupler portion 204 further includes a pair of alignment sockets; a first alignment socket 214 is defined in the floor surface 212, and a second alignment socket 216 is defined in the floor surface 212 in spaced relation from the first alignment socket 214. Each of the first alignment socket 214 and the second alignment socket 216 is a generally circular bore having a socket bore diameter 224. A bushing 218 may be disposed in each of the first alignment socket 214 and the second alignment socket 216 and may include a flange portion 220 having an inlet radius 222. The flange portion 220 limits an insertion depth of each bushing 218 into the respective alignment socket 214, 216. Additionally, and as will be discussed in further detail below, the flange portion 220 limits an insertion depth of the first coupler portion 202 when coupling the first coupler portion 202 to the second coupler portion 204. Similar to the alignment sockets 214, 216, each bushing 218 defines a circular bore having a bushing bore diameter (not shown in detail). It will be appreciated that in implementations of the coupling system 200 that utilize the bushings 218, the socket bore diameter 224 may be the same as the bushing bore diameter in order to accommodate the thickness of the bushing 218.

In addition to the alignment sockets 214, 216, a clamp aperture 226 may be defined in the floor surface 212 of the receiver 210. The clamp aperture 226 is configured for releasable engagement with the clamping mechanism 206 for biasing the first coupler portion 202 into engagement with the second coupler portion 204. Here, in the first exemplary implementation shown in FIG. 6, the clamp aperture 226 may be a threaded hole, and more specifically, the clamp aperture 226 may be a pair of clamp apertures 226. Each of the clamp apertures 226 may be realized as threaded holes (not shown in detail) arranged in spaced relation to each other. Here, the pair of threaded holes are spaced from each other and arranged between the first alignment socket 214 and the second alignment socket 216. Furthermore, the pair of clamp apertures 226 may be aligned with each other and spaced from the first and second alignment sockets 214, 216. More specifically, each of the clamp apertures 226 may have a centerpoint, and each of the first alignment socket 214 and the second alignment socket 216 may have a centerpoint (not shown in detail). A line extending between the centerpoints of the clamp apertures 226 and a line extending between the centerpoints of the first and second alignment sockets 214, 216 may be parallel to, and spaced from, one another (not shown in detail). The clamp apertures 226 may be spaced inwardly from the first and second alignment sockets 214, 216 relative to an exterior surface of the body 180 in some implementations. Other configurations are contemplated.

In addition to the floor surface 212, the receiver 210 may further an upper receiver wall 228 and a lower receiver wall 230 spaced therefrom. The upper and lower receiver walls 228, 230 are generally perpendicular to the floor surface 212 and extend along an insertion axis 232, along which the first coupler portion 202 is inserted into the second coupler portion 202. Here, the upper receiver wall 228 may be parallel to the lower receiver wall 230 forming a generally rectangular receiver 210. In other implementations the upper receiver wall 228 may be angled relative to the lower receiver wall 230. More specifically, the upper receiver wall 228 and the lower receiver wall 230 may be angled away from each other toward the outer surface of the body 180 to form a dovetail shaped receiver 210 with a dovetail shape to facilitate repeatable coupling of the coupling system 200 in some versions.

Turning now to FIGS. 9-12, the details of the first coupler portion 202 are shown. Specifically, the first coupler portion 202 may comprise a boss 240 coupled to the robotic arm 156 and protruding therefrom. The boss 240 includes a front face 242, an outer face 244, an inner face 246 opposite the outer face 244, an upper face 248, and a lower face 250 opposite the upper face 248. The outer face 244, inner face 246, upper face 248, and lower face 250 are each adjacent to the front face 242 and generally extend along the direction of the insertion axis 232. Said differently, the front face 242 is generally perpendicular to the insertion axis 232 and the outer face 244, inner face 246, upper face 248, and lower face 250 cooperate to define a perimeter of the front face 242.

The first coupler portion 202 may further comprise a mounting hub 252 fixedly coupled to the surgical robotic arm 156. The mounting hub 252 as illustrated herein is generally circular having an inner hub flange 254 oriented toward the robotic arm 156 and an outer hub flange 256. The generally circular shape of the mounting hub 252 defines a tilt axis 258 extending perpendicular to each of the inner hub flange 254 and the outer hub flange 256. A coupling flange 260 may be defined in the outer hub flange 256 and extend though the mounting hub 252 to the inner hub flange 254. The coupling flange 260 is engageable with the robotic arm 156 and receives one or more fasteners (not shown) for securing the first coupler portion 202 to the robotic arm 156.

As mentioned above, the mounting hub 252 defines the tilt axis 258, which extends outwardly from the mount end 162 of the robotic arm 156. Here, the term "inner" generally refers to a location closer to the robotic arm 156, and the term "outer" generally refers to a location further from the robotic arm 156 than the corresponding inner location. The tilt axis 258 is aligned with a rotary joint 262 of the robotic arm 156. The rotary joint 262 has a tilt motor (not shown) arranged in the mount end 162 of the robotic arm 156 configured to tilt the end effector 164 about an axis of rotation aligned with the tilt axis 258. The tilt motor comprises a rotor (not shown) arranged on the tilt axis 258, to which the coupling flange 260 is engaged for coupling the mounting hub 252.

Figure 11:
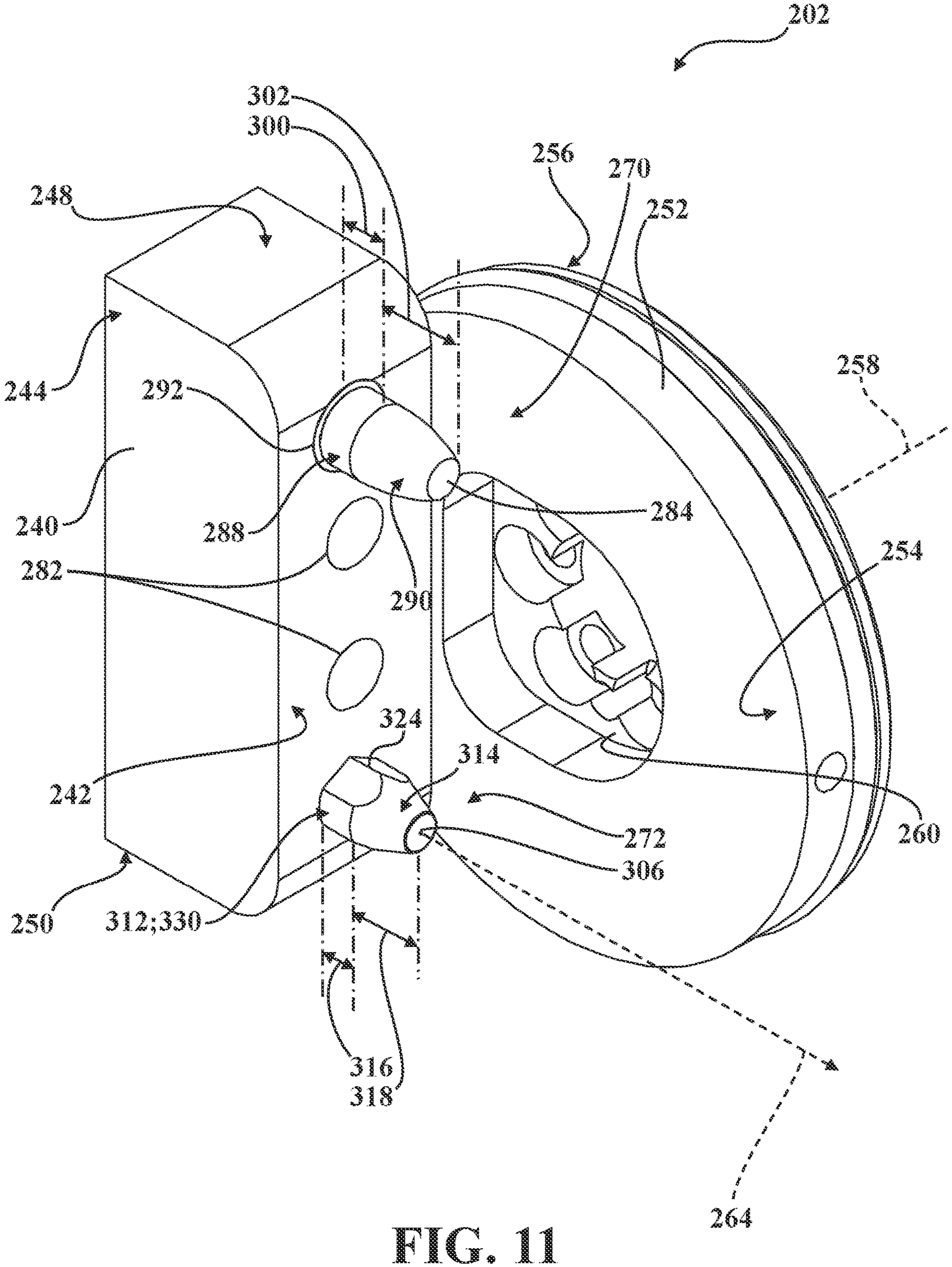
FIG. 11 is an enlarged perspective view of the first coupler portion showing a boss, a mounting hub, and first and second alignment pins.

The boss 240 of the first coupler portion 202 may be coupled to the robotic arm 156 through the mounting hub 252. Specifically, the inner face 246 of the boss 240 is engaged with the outer hub flange 256 of the mounting hub 252 such that boss 240 is protruding from the mounting hub 252 parallel to the tilt axis 258. The front face 242 may be parallel to and spaced from the tilt axis 258 as illustrated in FIG. 11. In the illustrated version, the insertion axis 232 and the tilt axis 258 are generally arranged at 90 degrees to one another.

The first coupler portion 202 further comprises a first alignment pin 270 and a second alignment pin 272 each extending from the front face 242 of the boss 240. Each of the first alignment pin 270 and the second alignment pin 272 are coupled to the boss 240 and protrude from the front face 242 in the first axial direction 264. The first alignment pin 270 and the second alignment pin 272 are arranged in spaced relation to each other for engagement with the respective first alignment socket 214 and second alignment socket 216 when the first coupler portion 202 is engaged with the second coupler portion 204. As will be discussed in further detail below, the first alignment pin 270 has a first configuration and the second alignment pin 272 has a second configuration different from the first configuration.

As mentioned above, the first coupler portion 202 is coupled to the second coupler portion 204. To this end, inserting the boss 240 into the receiver 210 in a first axial direction 264 along the insertion axis 232 engages the boss 240 with the socket body 208. The front face 242 of the boss 240 is oriented toward the floor surface 212 of the receiver 210, the upper face 248 of the boss 240 is engaged with the upper receiver wall 228 of the receiver 210, and the lower face 250 of the boss 240 is engaged with the lower receiver wall 230 of the receiver 210. As the front face 242 is moved toward the floor surface 212, the first alignment pin 270 is received in the corresponding first alignment socket 214 and the second alignment pin 272 is received in the corresponding second alignment socket 216.

In order to securely fasten the first coupler portion 202 to the second coupler portion 204, a first implementation of the clamping mechanism 206 comprises a clamp member 276 interposed between the first coupler portion 202 and the second coupler portion 204 for biasing the coupling system 200 into a coupled configuration. The clamp member 276 exerts a clamping force on the first coupler portion 202 toward the second coupler portion 204 to align and retain the first alignment pin 270 in the first alignment socket 214 and the second alignment pin 272 in the second alignment socket 216.

In one implementation of the coupling system 200, shown in FIGS. 5-12, the clamp member 276 comprises a first threaded fastener 278 and a second threaded fastener 280. Each of the first and second threaded fasteners 278, 280 has a clamped configuration CC, in which the clamping force is acting between the first and second coupler portions 202, 204; and an unclamped configuration UC, in which the clamping force between the first and second coupler portions 202, 204 is removed to allow the end effector 164 to be removed from the robotic arm 156. In another implementation of the clamping mechanism 406 (discussed below), shown in FIGS. 13-17, the clamp member 476 is pivotable between the clamped configuration CC and the unclamped configuration UC for engagement with a toggle fastener 478.

Figure 12:
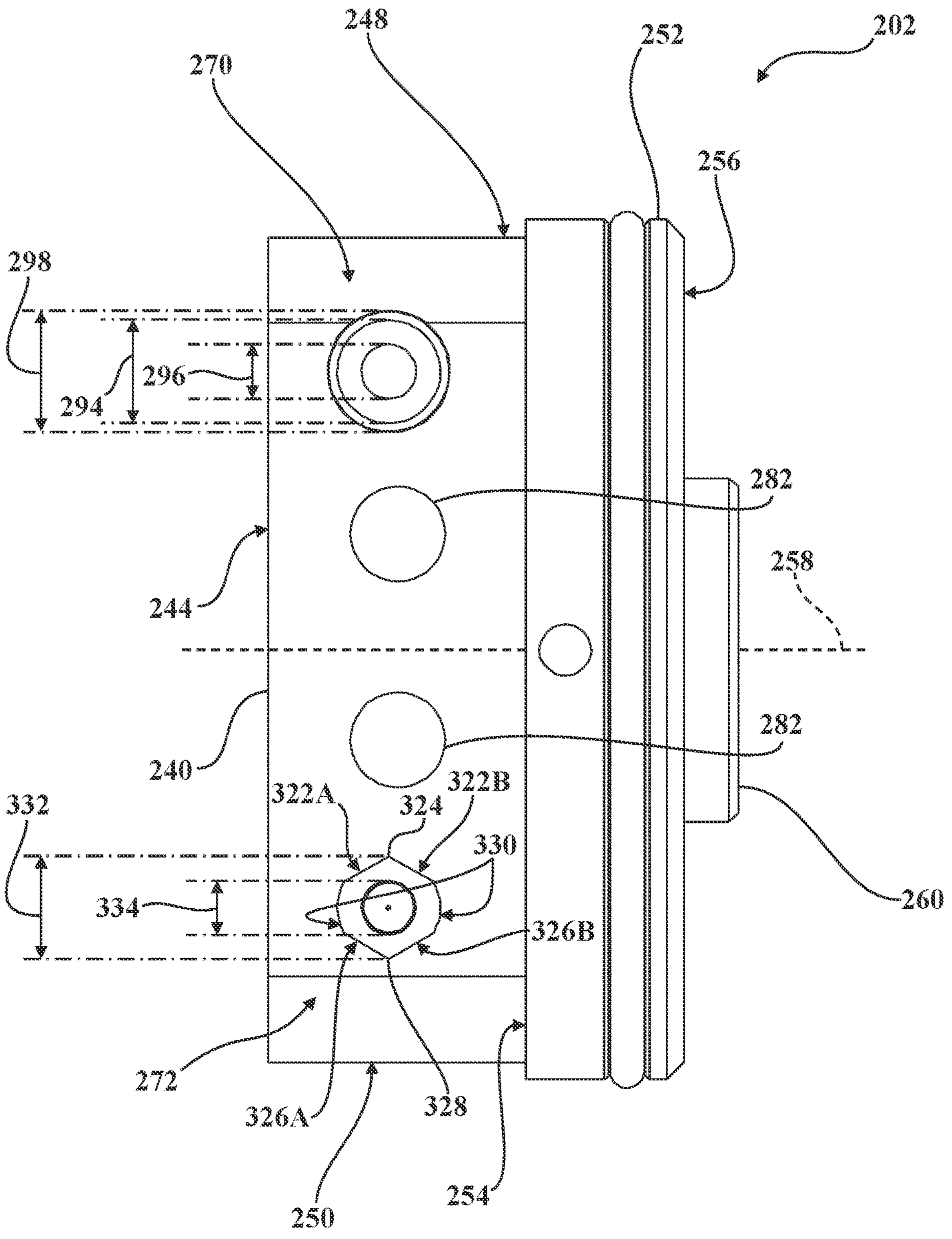
FIG. 12 is a front-side view of the first coupler portion of FIG. 11 showing the boss, the mounting hub, and the first and second alignment pins.
Figure 13:
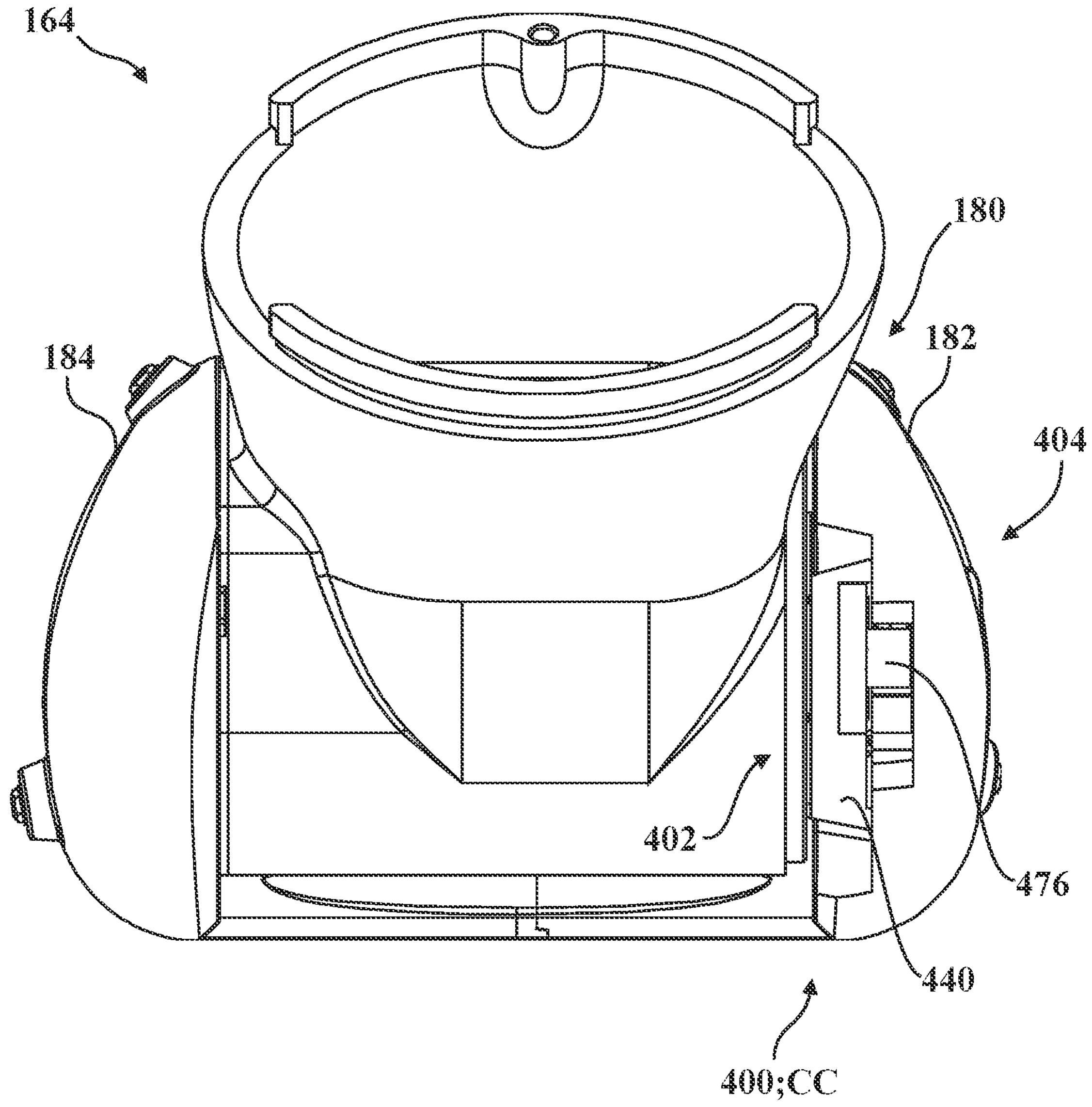
FIG. 13 is a rear side view of the mount end of the robotic arm and an end effector having a second implementation of a coupling system having a first coupler portion and a second coupler portion for removing the end effector from the robotic arm.

With renewed reference to FIGS. 11 and 12, the boss 240 may define one or more tension holes 282 extending therethrough in a direction parallel to the first axial direction 264. Here, the one or more tension holes 282 are configured to receive the clamp member 276, and in this exemplary implementation each of the tension holes 282 receives one of the threaded fasteners 278, 280. Furthermore, the arrangement of the tension holes 282 on the front face 242 of the boss 240 corresponds to the arrangement of the clamp apertures 226 in the floor surface 212. The tension holes 282 are arranged vertically between the first alignment pin 270 and the second alignment pin 272. In this way, when the boss 240 is received in the receiver 210 each of the tension holes 282 is aligned with one of the clamp apertures 226 such that a threaded fasteners 278 received in one of the tension holes 282 with engage the corresponding clamp aperture 226 for clamping the first coupler portion 202 to the second coupler portion 204. As shown in FIG. 12, each of the tension holes 282 may have a centerpoint, and each of the first alignment pin 270 and the second alignment pin 272 may have a centerpoint (not shown in detail). A line extending between the centerpoints of the tension holes 282 and a line extending between the centerpoints of the first and second alignment pins 270, 272 may be parallel to, and spaced from, one another (not shown in detail). The tension holes 282 may be spaced inwardly from the first and second alignment pins 270, 272 relative to the outer face 244 of the boss 240 in some implementations. Other configurations are contemplated.

As mentioned above, the first alignment pin 270 has a first configuration and the second alignment pin 272 has a second configuration different from the first configuration. Said differently, the physical configuration of the first alignment pin 270 is different from the second alignment pin 272. Here, physical configuration refers to properties such as size and shape, however in some implementations the configuration may refer to other differences such as material, arrangement, quantity, etc. While the first alignment pin 270 is shown arranged nearer to the upper face 248 of the boss 240 and the second alignment pin 272 is shown arranged nearer to the lower face 250 in this implementation, it should be appreciated that their respective locations may be interchanged.

With respect to the first alignment pin 270, the first configuration is defined as a cylinder extending in the first axial direction 264 between the boss 240 and a first pin end 284 with a first pin length 286 defined between the boss 240 and the first pin end 284. The first alignment pin 270 comprises a first portion 288 and a second portion 290, the first portion 288 arranged proximate to the front face 242 and the second portion 290 is arranged proximate to the first pin end 284. The first alignment pin 270 may further comprise a pin stop 292 adjacent to the front face 242. Each of the first portion 288, the second portion 290, and the pin stop 292 has a cross-sectional shape that is generally circular, with the center of each of those circles aligned with one another. The pin stop 292 has a diameter 298 greater than the proximal pin diameter 294, which is also greater than the socket bore diameter 224. Because the pin stop diameter 298 is greater than the socket bore diameter 224, the pin stop 292 cannot be inserted into the first alignment socket 214, and thereby prevents the boss 240 from being further inserted into the receiver 210 and defines a fully engaged position of the first coupler portion 202 and the second coupler portion 204.

Engagement between the first alignment pin 270 and the first alignment socket 214 constrains the position of the second coupler portion 204 (relative to the first coupler portion 202) in five degrees of freedom (DOF). The engagement between the first alignment pin 270 and the first alignment socket 214 has one degree of freedom, rotation about the centerline of the first alignment pin 270. More specifically, the contact between the circular outer surface of the first portion 288 of the first alignment pin 270 and the inner surface of the first alignment socket 214 prevents relative translation along two axes and relative rotation about two axes. When the coupling system 200 is in the fully engaged position with the boss 240 seated in the receiver 210, the pin stop 292 may engage the floor surface 212, or as shown here the flange portion 220 of the bushing 218, to prevent further insertion and constrain an additional degree of freedom. It should be appreciated that this degree of freedom is constrained when the clamping mechanism 206 is in the clamped configuration CC with the clamp member 276 engaged with the socket body 208. When the clamping mechanism 206 is in the unclamped configuration UC the first alignment pin 270 may be translated and removed from the first alignment socket 214 for disassembly.

Each of the first portion 288 and the second portion 290 defines a corresponding length: the first portion 288 having a first portion length 300 and the second portion 290 having a second portion length 302. In the exemplary implementation illustrated herein, the first portion length 300 is less than the second portion length 302. However, the first configuration may be configured such that the first portion length 300 is equal to, or greater than, the second portion length 302. The first portion 288 of the first alignment pin 270 has a proximal pin diameter 294, which is approximately equal to the socket bore diameter 224 of the bushing 218. The diameter of the second portion 290 tapers from the first portion 288, where it is approximately equal to the proximal pin diameter 294, to the first pin end 284, which has a pin end diameter 296. Said differently, the second portion 290 of the first alignment pin 270 is tapered between the first portion 288 and the first pin end 284. In the exemplary first configuration illustrated herein, the taper is non-linear, or "bullet shaped". The non-linear taper of the second portion 290 facilitates smooth engagement between the first alignment pin 270 and the first alignment socket 214. Because the diameter of the second portion 290 is less than the proximal pin diameter 294 of the first portion 288 (and the socket bore diameter 224), the second portion 290 is more easily aligned with, and inserted into, the first alignment socket 214. Alternatively, other taper configurations are contemplated, such as linear (e.g., chamfered), ball-shaped, stepped (e.g., "bull-nose"), radius, etc.

With continued reference to FIG. 11, the second alignment pin 272 is shown having the second configuration. The second configuration is defined as a rod extending in the first axial direction 264 between the boss 240 and a second pin end 306, wherein an outer surface of the rod comprises two edges parallel to the first axial direction 264. Similar to above, the second alignment pin 272 has a first portion 312 and a second portion 314, each defining a corresponding first portion length 316 and second portion length 318. The first portion 312 is arranged proximate to the front face 242 of the boss 240 and the second portion 314 is arranged proximate to the second pin end 306. In the exemplary implementation illustrated herein, the first portion length 316 is approximately equal to the second portion length 318. However, the second configuration may be configured such that the first portion length 316 is less than, or greater than, the second portion length 318. The second alignment pin 272 further has a second pin length 320, which is defined between the front face 242 of the boss 240 and the second pin end 306.

The second configuration of the second alignment pin 272 may comprise four pin surfaces 322A, 322B, 326A, 326B which form the outer surface: an upper adjacent pair 322A, 322B and a lower adjacent pair 326A, 326B. The upper adjacent pair of pin surfaces 322A, 322B intersect to define a first edge 324. Similarly, the lower adjacent pair of pin surfaces 326A, 326B intersect to define a second edge 328. The upper adjacent pair of pin surfaces 322A, 322B are arranged on an opposing side (or half) of the outer surface than the lower adjacent pair of pin surfaces 326A, 326B. Said differently, the upper adjacent pair 322A, 322B is arranged opposite to the lower adjacent pair 326A, 326B and across a centerline of the second alignment pin 272. The second alignment pin 272 may further comprise two rounded surfaces 330, each rounded surface 330 arranged between the upper adjacent pair 322A, 322B and the lower adjacent pair 326A, 326B. More specifically, each rounded surface 330 may be adjacent to both the upper adjacent pair 322A, 322B and the lower adjacent pair 326A, 326B. One of the rounded surfaces 330 is adjacent to upper pin surface 322A and lower pin surface 326A, and the other of the rounded surfaces 330 is adjacent to upper pin surface 322B and lower pin surface 326B.

The second configuration of the second alignment pin 272 may be defined by a second pin diameter 332, similar to the first alignment pin 270. Accordingly, the second pin diameter 332 is approximately equal to the socket bore diameter 224 of the second alignment socket 216. In some implementations, the second pin diameter 332 may be the same as the proximal pin diameter 294 of the first alignment pin 270. The second pin diameter 332 may be defined between the first edge 324 and the second edge 328, or alternatively, the second pin diameter 332 may correspond to a radius measurement between one of the first and second edges 324, 328, and a centerline of the second alignment pin 272. The rounded surfaces 330 may also be defined by the second pin diameter 332. Each of the rounded surfaces 330 are segments of a circle defined by the second pin diameter 332. Said differently, the rounded surfaces 330 may have a radius, measured from the centerline of the second alignment pin 272, that is equal to half of the second pin diameter 332. Each of the pin surfaces 322A, 322B, 326A, 326B is within the second pin diameter 332 (i.e., spaced closer to the centerline) and therefore do not engage or contact the inner surface of the second alignment socket 216 when the second alignment pin 272 is inserted.

The second pin end 306 of the second alignment pin 272 may be defined by a pin end diameter 334, which is less than the second pin diameter 332. To transition from the second pin diameter 332 to the pin end diameter 334, a portion of the second alignment pin 272 includes a tapered portion (not shown in detail). Here, the second portion 314 of the second alignment pin 272 comprises an angled surface, which is tapered between the second pin diameter 332 and the pin end diameter 334 (not shown in detail). The exemplary implementation of the second alignment pin 272 illustrated herein is configured with a second portion 314 having a linear taper between the second pin diameter 332 and the pin end diameter 334. As with above, other taper configurations are contemplated, such as non-linear (e.g., "bullet-shaped"), ball-shaped, stepped (e.g., "bull-nose"), radius, etc.

Similar to the first alignment pin 270, engagement between the second alignment pin 272 and the second alignment socket 216 constrains the position of the second coupler portion 204 (relative to the first coupler portion 202) in four degrees of freedom (DOF). The engagement between the second alignment pin 272 and the second alignment socket 216 has two degrees of freedom, rotation about the centerline of the second alignment pin 272 and translation along the insertion axis 232. More specifically, the contact between the first and second edges 324, 326, the rounded surfaces 330, and the inner surface of the second alignment socket 216 prevents relative translation along two axes and relative rotation about two axes.

As mentioned above, the second alignment pin 272 has a second pin length 320, and the first alignment pin 270 has a first pin length 286. Best shown in FIGS. 6 and 11, the second pin length 320 may be less than the first pin length 286. As a result, when the boss 240 is inserted into the receiver 210 along the insertion axis 232, the first alignment pin 270 is received in the corresponding first alignment socket 214 before the second alignment pin 272 is received in the corresponding second alignment socket 216. Said differently, a distance between the front face 242 of the boss 240 and the floor surface 212 of the receiver 210 when the first pin end 284 of the first alignment pin 270 is received in the first alignment socket 214 than when the second pin end 306 of the second alignment pin 272 is received in the second alignment socket 216. Sequential engagement between the alignment pins 270, 272 and the respective alignment sockets 214, 216 makes coupling the first coupler portion 202 and the second coupler portion 204 easier by allowing for a greater degree of misalignment during assembly. Said differently, because there is initially less engagement and fewer points of contact between the first coupler portion 202 and the second coupler portion 204, the relative position is less constrained, enabling the user to align the first coupler portion 202 and the second coupler portion 204 more easily.

To this end, the engagement between the first alignment pin 270 and the first alignment socket 214 has a first surface area, which is approximately equal to an outer surface area of the first portion 288 of the first alignment pin 270. Similarly, the engagement between the second alignment pin 272 and the second alignment socket 216 has a second surface area. As mentioned above, the pin surfaces 322A, 322B, 326A, 326B do not engage the second alignment socket 216, whereas as the first and second edges 324, 326 and the rounded surfaces 330 engage the second alignment socket 216. As such, second surface area is approximately equal to the surface area of the rounded surfaces 330 and the surface area of the edges 324, 326. The first surface area is greater than the second surface area. Said differently, the first engagement pin 270 has a larger area of contact with the first alignment socket 214 than area of contact of the second alignment pin 272 with the second alignment socket 216. It should be appreciated that the area of contact measurements are approximate and may vary according to normal manufacturing tolerances of each of the components.

Turning now to FIGS. 13-17, the second implementation of the clamping mechanism 406 is shown configured with the mount end 162 of the robotic arm 156 and the end effector 164. As mentioned above, in this implementation of the clamping mechanism 406 the clamp member 476 is pivotable between the clamped configuration CC (FIG. 14A) and the unclamped configuration UC (FIG. 14B) for engagement with the toggle fastener 478. Here, the first coupler portion 402 may similarly comprise a boss 440 coupled to the robotic arm 156 and protruding therefrom. The boss 440 includes an outer face 444, an inner face 446 opposite the outer face 444, an upper face 448, and a lower face 450 opposite the upper face 448. The upper face 448 and the lower face 450 are configured at an angle to one another to form a dovetail arrangement engageable with the second coupler portion 404. The toggle fastener 478 is coupled to the outer face 444 of the boss 440 and protrudes in an outward direction. The toggle fastener 478 has a generally cylindrical configuration and is engageable with the clamp member 476 for clamping the boss 440 into engagement with a socket body 408.

The first coupler portion 402 may further comprise a mounting hub 452 fixedly coupled to the surgical robotic arm 156. The mounting hub 452 as illustrated herein is generally circular having an inner hub flange 454 oriented toward the robotic arm 156 and an outer hub flange 456. The generally circular shape of the mounting hub 452 defines a tilt axis 458 extending perpendicular to each of the inner hub flange 454 and the outer hub flange 456. A coupling flange 460 may be defined in the outer hub flange 456 and extend though the mounting hub 452 to the inner hub flange 454. The coupling flange 460 is engageable with the robotic arm 156 and receives one or more fasteners (not shown) for securing the first coupler portion 202 to the robotic arm 156.

The second coupler portion 404 comprises the socket body 408, which defines a receiver 410. The receiver 410 may comprise three walls, an upper receiver wall 428, a lower receiver wall 430 spaced therefrom, and an outer receiver wall 432 extending between each of the upper receiver wall 428 and the lower receiver wall 430. Each of the upper and lower receiver walls 428, 430 are configured at an angle to one another to form the complementary dovetail arrangement engageable with the first coupler portion 402. A toggle recess 434 is further defined in the socket body 408 and outwardly offset from the outer receiver wall 432. The clamp member 476 is pivotably supported in the toggle recess 434 for movement between the clamped configuration CC and the unclamped configuration UC.

Figure 14A:
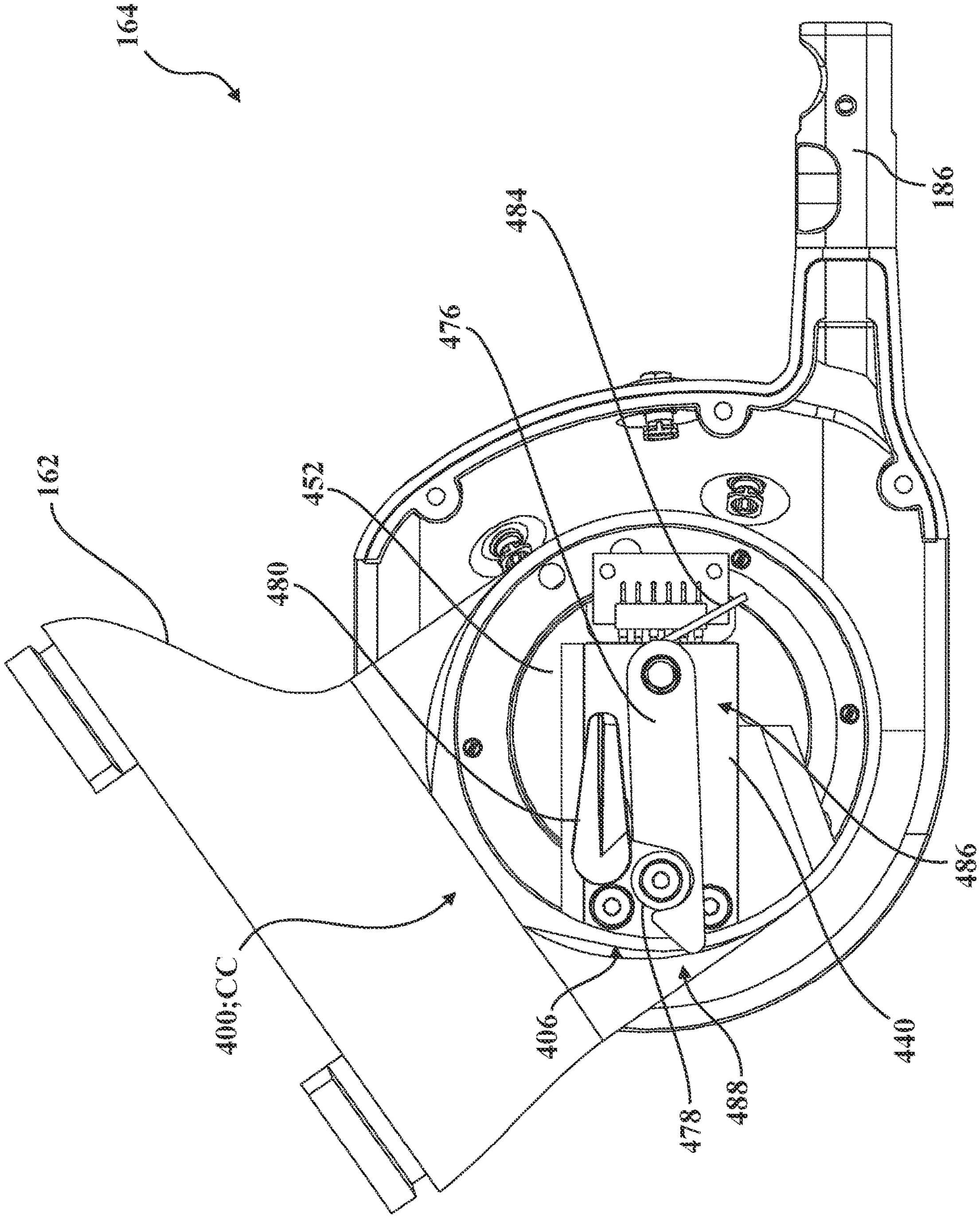
FIG. 14A is a side view of the end effector of FIG. 13 with a body portion hidden and showing the first coupler portion and a clamping member in a clamped configuration of the coupling system.
Figure 14B:
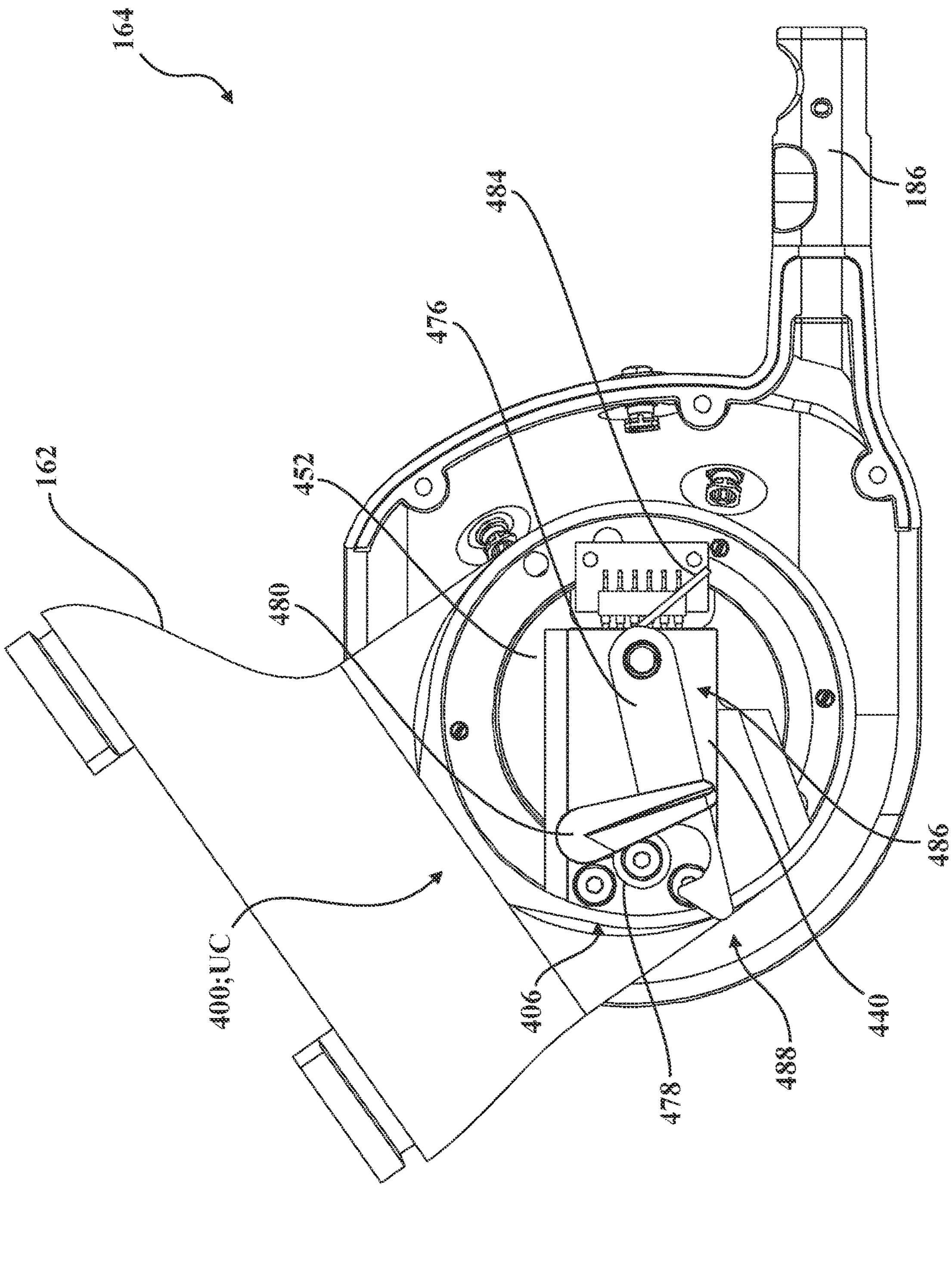
FIG. 14B is another side view of the end effector of FIG. 13 with the body portion hidden and showing the first coupler portion and the clamping member in an unclamped configuration of the coupling system.
Figure 15:
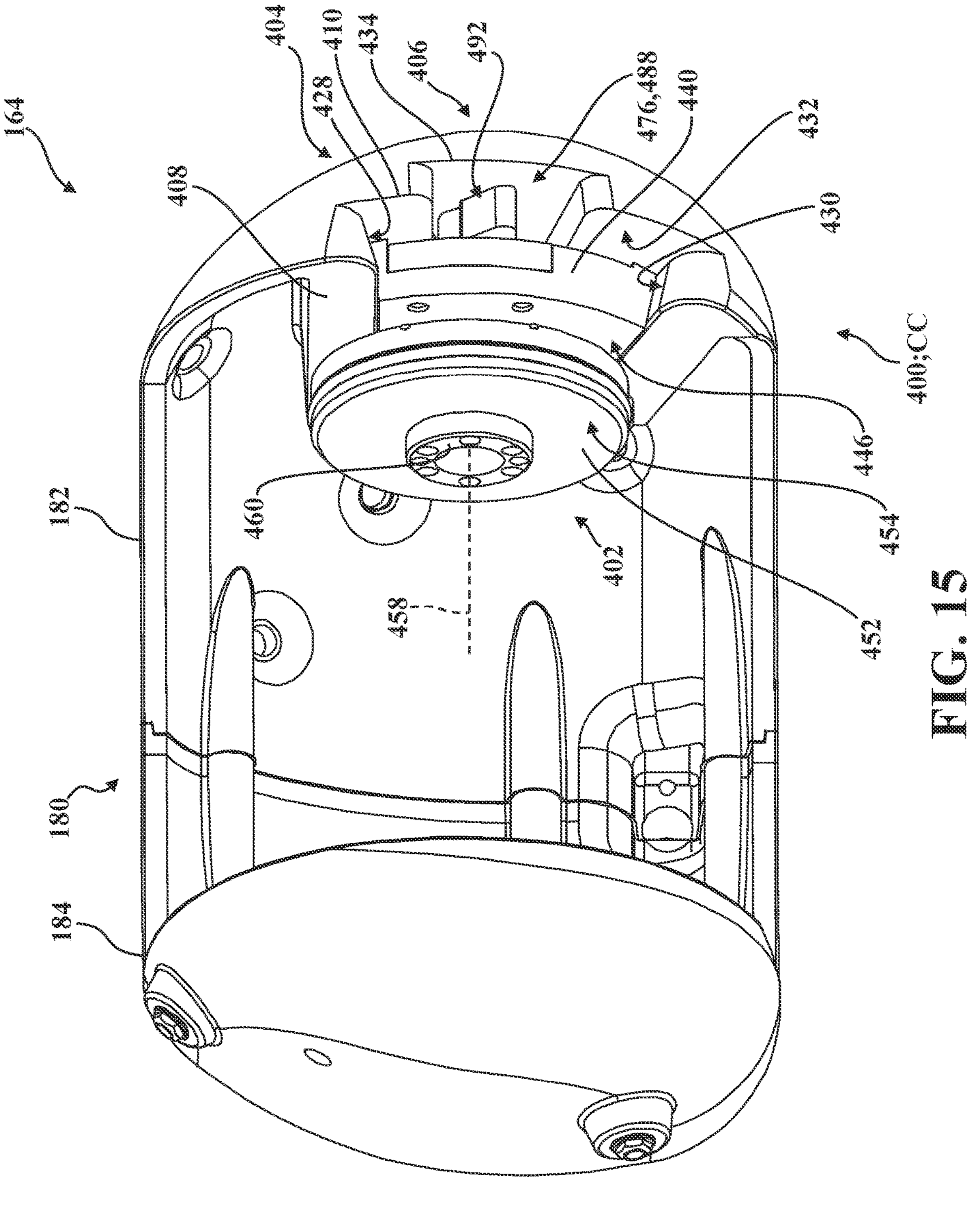
FIG. 15 is a rear-side perspective view of the end effector, the first coupler portion engaged with the second coupler portion, and the clamping member in the clamped configuration.
Figure 16:
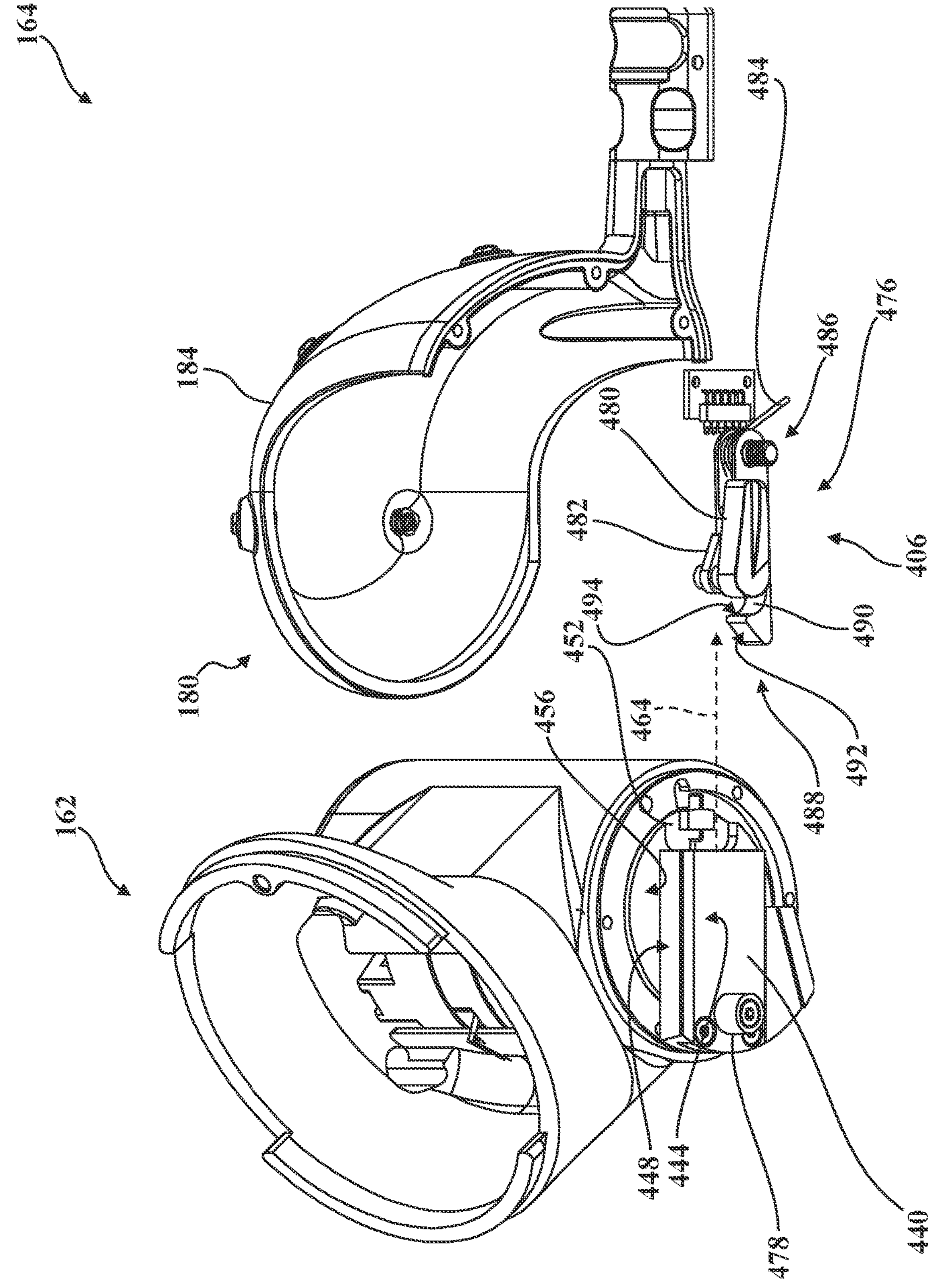
FIG. 16 is a partially exploded top-side perspective view of the end effector, the first coupler portion, and the clamping member.
Figure 17:
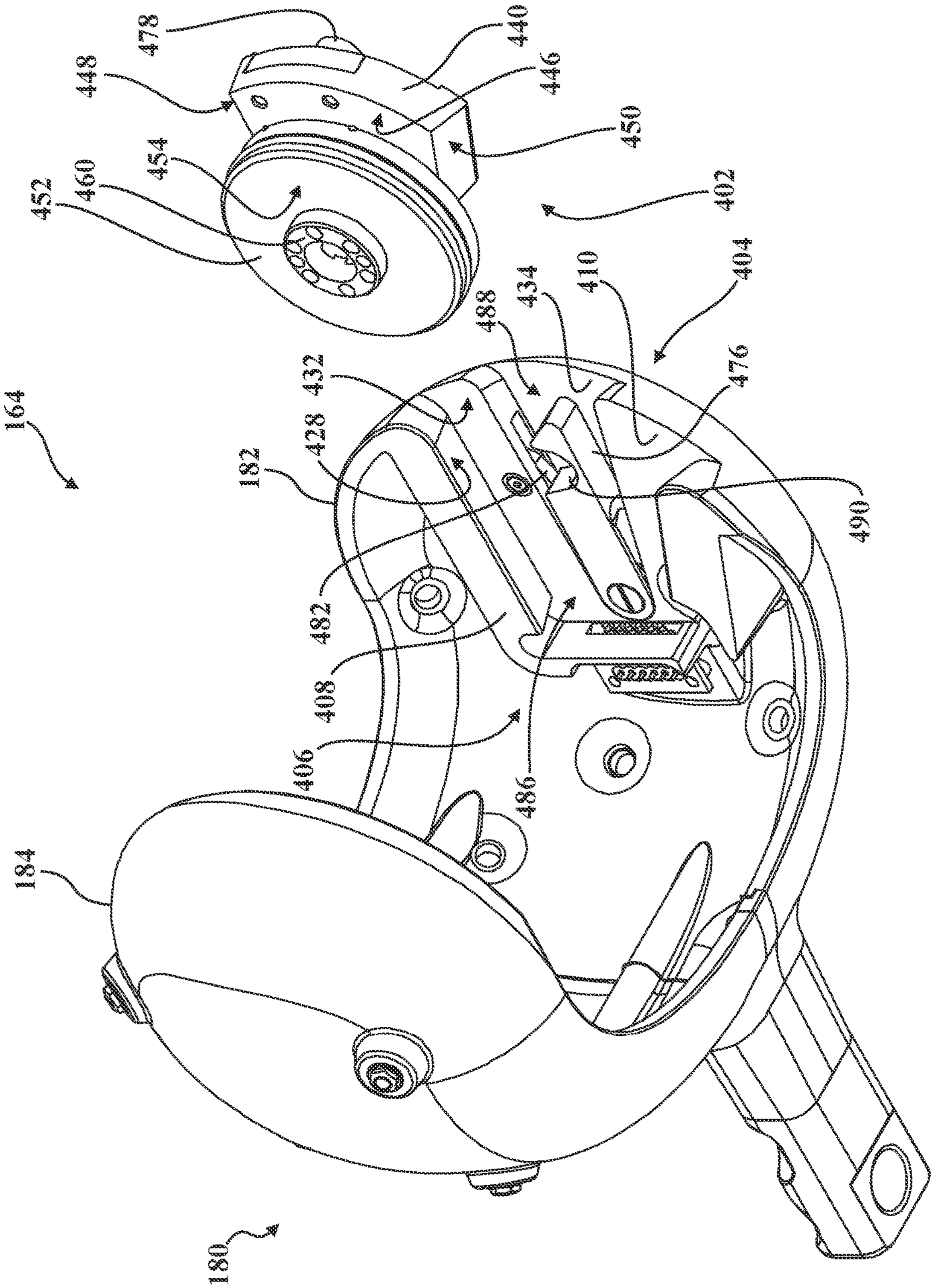
FIG. 17 is a partially exploded rear-side perspective view of the end effector, the first coupler portion, the second coupler portion, and the clamping member.

FIGS. 14A, 14B, and 16 additional components of the clamping mechanism 406 are shown. Specifically, the clamping mechanism 406 may further comprise an actuator 480, a cam member 482, and a return spring 484. The actuator 480 is pivotably supported in the body 180 of the end effector 164 and operable by the user to move the clamping mechanism 406 into the unclamped configuration UC in furtherance of removing the end effector 164 from the surgical robotic arm 156. The cam member 482 is arranged adjacent to the toggle recess 434 and coupled to the actuator 480 for pivoting movement therewith. The cam member 482 is operably engaged with the clamp member 476 to pivot the clamp member 476 within the toggle recess 434.

The clamp member 476 may extend between a first portion 486 and an opposing hook portion 488. The hook portion 488 defines a mouth 490 sized to receive the toggle fastener 478 and has a first angled hook face 492. The hook portion 488 may further have a second angled hook face 494 oriented away from the first angled hook face 492 at one end of the clamp member 476. Both the first angled hook face 492 and the second angled hook face 494 are at an angle relative to the first axial direction 464, as will be discussed below. The first portion 486 of the clamp member 476 is pivotably supported by the body 180 of the end effector 164 such that pivoting movement of the clamp member 476 causes the hook portion 488 to move in a circular path relative to the first portion 486. The return spring 484 in the exemplary implementation as illustrated herein may arranged adjacent to the first portion 486 of the clamp member 476 for engagement therewith. The return spring 484 is configured to store potential energy and to bias the clamp member 476 toward the clamped configuration CC. More specifically the return spring 484 urges the hook portion 488 toward the upper receiver wall 428.

The clamp member 476 exerts a clamping force on the first coupler portion 402 toward the second coupler portion 404 to align and retain the boss 440 in the receiver 410. More specifically, when the boss 440 is inserted in the receiver 410, the upper face 448 and the lower face 450 engage the corresponding upper receiver wall 428 and lower receiver wall 430 to initially align the first coupler portion 402. Continued movement of the boss 440 into the receiver 410 in the first axial direction 464 moves the toggle fastener 478 toward and into contact with the second angled hook face 494. Because the second angled hook face 494 is at an angle relative to the first axial direction 464, further engagement between the toggle fastener 478 and the second angled hook face 494 causes the clamp member 476 to pivot toward the unclamped configuration UC until toggle fastener 478 can pass between the hook portion 488 and the upper receiver wall 428 of the receiver 410 and into the mouth 490 for engagement with the first angled hook face 492. Because the first angled hook face 492 is at an angle relative to the first axial direction 464, the pivoting force exerted by the return spring 484 on the clamp member 476 is converted to a clamping force on the first coupler portion 402 by engagement between the toggle fastener 478 and the first angled hook face 492. The angle of the first angled hook face 492 urges the boss 440 into the receiver 410 to securely fasten the first coupler portion 402 to the second coupler portion 404.

When the coupling system 400 is in the clamped configuration CC and the user desires to remove the end effector 164 from the robotic arm 156, the user actuates, or pivots, the actuator 480, which in turn pivots the cam member 482. As the cam member 482 pivots, the distance between a point of contact with the clamp member 476 at an outmost surface of the cam member 482 a pivot axis of the cam member 482 increases, which causes the clamp member 476 to move toward the unclamped configuration UC. In the unclamped configuration UC the toggle fastener 478 is disengaged from the first angled hook face 492 and spaced from the mouth 490 of the hook portion 488. The user is then able to slide the second coupler portion 404 away from the first coupler portion 402 to separate the boss 440 from the receiver 410, thereby decoupling the end effector 164. When the user releases the actuator 480 the return spring 484 biases the hook portion 488 of the clamp member 476 back toward the upper receiver wall 428.

Several instances have been discussed in the foregoing description. However, the aspects discussed herein are not intended to be exhaustive or limit the disclosure to any particular form. Various modifications to these aspects will be readily apparent to those skilled in the art, and the generic principles defined herein may be applied to other aspects without departing from the scope of the disclosure. The terminology that has been used is intended to be in the nature of words of description rather than of limitation. Many modifications and variations are possible in light of the above teachings and the disclosure may be practiced otherwise than as specifically described.

What is claimed is:

1. A coupling system for removably attaching an end effector to a distal end of a surgical robotic arm, the coupling system comprising:

a first coupler portion including:

a boss coupled to the robotic arm;

a first alignment pin extending from the boss and having a first configuration;

a mounting hub fixedly coupled to the surgical robotic arm and wherein the mounting hub defines a tilt axis aligned with a rotary joint of the surgical robotic arm, and wherein the boss protrudes parallel to the tilt axis; and a second alignment pin extending from the boss in spaced relation from the first alignment pin and having a second configuration different from the first configuration;

a second coupler portion engageable with the first coupler portion to tilt about an axis of rotation aligned with the tilt axis, the second coupler including:

a socket body defining a receiver with a floor surface, wherein the tilt axis is perpendicular to a first axial direction along which the boss is configured to engage with the receiver;

a first alignment socket defined in the floor surface;

a second alignment socket defined in the floor surface in spaced relation from the first alignment socket; and a clamp mechanism operatively engageable between the first coupler portion and the second coupler portion and movable between a clamped configuration with the first alignment pin engaged with the first alignment socket and the second alignment pin engaged with the second alignment socket for securing the first coupler portion to the second coupler portion.

2. The coupling system of claim 1, wherein the first coupler portion is coupled to the surgical robotic arm and the second coupler portion is coupled to the end effector.

3. The coupling system of claim 1, wherein a tension hole is defined in the boss and extends in a first axial direction therethrough.

4. The coupling system of claim 3, wherein the tension hole is arranged between the first alignment pin and the second alignment pin.

5. The coupling system of claim 4, wherein a center of the tension hole is spaced from a line extending between a center of the first alignment pin and a center of the second alignment pin.

6. The coupling system of claim 1, wherein the first configuration of the first alignment pin is defined as a cylinder extending in a first axial direction between the boss and a first pin end, wherein a first length is defined between the boss and the first pin end.

7. The coupling system of claim 6, wherein the second configuration of the second alignment pin is defined as a rod extending in the first axial direction between the boss and a second pin end, wherein an outer surface of the rod comprises two edges parallel to the first axial direction.

8. The coupling system of claim 7, wherein a second length is defined between the boss and the second pin end, and wherein the second length is less than the first length of the first alignment pin.

9. The coupling system of claim 7, wherein the second alignment pin comprises, an upper adjacent pair of pin surfaces and a lower adjacent pair of pin surfaces, wherein the upper adjacent pair intersect to define a first edge and the lower adjacent pair intersect to define a second edge.

10. The coupling system of claim 9, wherein the upper adjacent pair and the lower adjacent pair are arranged on opposing sides of the second alignment pin.

11. The coupling system of claim 9, wherein two rounded surfaces are arranged between the upper adjacent pair and the lower adjacent pair.

12. The coupling system of claim 1, wherein engagement between the first alignment pin and the first alignment socket has a first surface area and engagement between the second alignment pin and the second alignment socket has a second surface area, and wherein the first surface area is greater then the second surface area.

13. The coupling system of claim 1, wherein the boss comprises a front face with the first alignment pin protruding from the front face further than the second alignment pin such that the first alignment pin engages the first alignment socket prior to the second alignment pin engaging the second alignment socket when the boss is engaged with the socket body and the front face moved toward the floor surface.

* * * * *